US012371421B2

(12) United States Patent
Vasbinder et al.

(10) Patent No.: US 12,371,421 B2
(45) Date of Patent: Jul. 29, 2025

(54) SOLID FORMS OF A PARP7 INHIBITOR

(71) Applicant: Ribon Therapeutics, Inc., Cambridge, MA (US)

(72) Inventors: Melissa Marie Vasbinder, Newton, MA (US); Laurie B. Schenkel, Somerville, MA (US); Kerren Kalai Swinger, Lexington, MA (US); Kevin Wayne Kuntz, Woburn, MA (US); Jun Xu, Hangzhou (CN); Meng Jiang, Suzhou (CN); Xin He, Suzhou (CN)

(73) Assignee: Ribon Therapeutics, Inc., Cambridge, MA (US)

( * ) Notice: Subject to any disclaimer, the term of this patent is extended or adjusted under 35 U.S.C. 154(b) by 943 days.

(21) Appl. No.: 17/607,090

(22) PCT Filed: Apr. 28, 2020

(86) PCT No.: PCT/US2020/030263
§ 371 (c)(1),
(2) Date: Oct. 28, 2021

(87) PCT Pub. No.: WO2020/223229
PCT Pub. Date: Nov. 5, 2020

(65) Prior Publication Data
US 2022/0162196 A1    May 26, 2022

(30) Foreign Application Priority Data

Apr. 29, 2019  (WO) ................ PCT/CN2019/084914

(51) Int. Cl.
C07D 403/14    (2006.01)
A61P 35/00    (2006.01)

(52) U.S. Cl.
CPC ............ *C07D 403/14* (2013.01); *A61P 35/00* (2018.01)

(58) Field of Classification Search
CPC ............................. C07D 403/14; A61P 35/00
See application file for complete search history.

(56) References Cited

U.S. PATENT DOCUMENTS

| | | |
|---|---|---|
| 6,432,632 B2 | 8/2002 | Nakayama et al. |
| 7,875,621 B2 | 1/2011 | Van Der Aa et al. |
| 10,189,831 B2 | 1/2019 | Arrington et al. |
| 10,550,105 B2 | 2/2020 | Vasbinder et al. |
| 10,870,641 B2 | 12/2020 | Vasbinder et al. |
| 11,014,913 B2 | 5/2021 | Vasbinder et al. |
| 11,293,927 B2 | 4/2022 | Wigle et al. |
| 11,566,020 B1 | 1/2023 | Vasbinder et al. |
| 11,691,969 B2 | 7/2023 | Peri et al. |
| 2003/0082665 A1 | 5/2003 | Ingraham et al. |
| 2004/0115710 A1 | 6/2004 | Li et al. |
| 2008/0161280 A1 | 7/2008 | Gandhi et al. |
| 2009/0176765 A1 | 7/2009 | Jones et al. |
| 2012/0258180 A1 | 10/2012 | Giranda et al. |
| 2015/0166544 A1 | 6/2015 | Zhang et al. |
| 2015/0182490 A1 | 7/2015 | Brown et al. |
| 2019/0330194 A1 | 10/2019 | Vasbinder et al. |
| 2019/0331688 A1 | 10/2019 | Wigle et al. |
| 2020/0109123 A1 | 4/2020 | McCann |
| 2020/0123134 A1 | 4/2020 | Vasbinder et al. |
| 2021/0024470 A1 | 1/2021 | Smits et al. |
| 2021/0024502 A1 | 1/2021 | Vasbinder et al. |
| 2021/0130342 A1 | 5/2021 | Perl et al. |
| 2022/0206008 A1 | 6/2022 | Wigle et al. |
| 2023/0192664 A1 | 6/2023 | Vasbinder et al. |
| 2024/0034728 A1 | 2/2024 | Peri et al. |

FOREIGN PATENT DOCUMENTS

| | | |
|---|---|---|
| CA | 2653529 | 12/2007 |
| CA | 2653529 C | 2/2016 |
| CN | 101501006 A | 8/2009 |
| CN | 101855221 A | 10/2010 |
| CN | 112424188 A | 2/2021 |
| ES | 2524787 T3 | 12/2014 |
| ES | 2548353 | 10/2015 |
| JP | 2009/538896 | 11/2009 |
| JP | 2011/503166 | 1/2011 |
| JP | 2011/515450 | 5/2011 |
| JP | 2013/502424 | 1/2013 |
| JP | 2015/527336 | 9/2015 |
| JP | 2016/512239 | 4/2016 |
| JP | 2018/535229 | 11/2018 |
| JP | 2021-145986 A | 9/2021 |
| JP | 6942896 B | 9/2021 |
| JP | 7518049 B2 | 7/2024 |
| TW | I361188 | 4/2012 |
| WO | WO 2003/027078 A1 | 4/2003 |
| WO | WO 2003/027097 A1 | 4/2003 |

(Continued)

OTHER PUBLICATIONS

International Preliminary Report on Patentability in International Appln. No. PCT/US2020/057819, dated May 3, 2022, 6 pages.
International Preliminary Report on Patentability in International Appln. No. PCT/US2020/057831, dated May 3, 2022, 6 pages.
"Acute Leukemia," Merck Manual (Online Edition), available on or before Jul. 10, 2013, 6 pages.
Amin et al. "A Novel Class of Substituted Spiro [Quinazoline-2,1í-Cyclohexane] Derivatives as Effective PPAR-1 Inhibitors: Molecular Modeling, Synthesis, Cytotoxic and Enzyme Assay Evaluation," Acta Poloniae Pharmaceutica, 2013 年, 70(4):687-708.
Barbarulo et al, "Poly(ADP-ribose) polymerase family member 14 (PARP14) is a novel effector of the JNK2-dependent pro-survival signal in multiple myeloma," Oncogene, 2013, 4231-4242.

(Continued)

*Primary Examiner* — John S Kenyon
*Assistant Examiner* — Sara Elizabeth Bell
(74) *Attorney, Agent, or Firm* — Fish & Richardson P.C.

(57) ABSTRACT

The present invention relates to solid forms of the poly (ADP-ribose) polymerase 7 (PARP7) inhibitor 5-[[(2S)-1-(3-oxo-3-[4-[5-(trifluoromethyl)pyrimidin-2-yl]piperazin-1-yl]propoxy)propan-2-yl]amino]-4-(trifluoromethyl)-2,3-dihydropyridazin-3-one, and salts thereof, including methods of preparation thereof, where the inhibitor is useful in the treatment of cancer.

20 Claims, 11 Drawing Sheets

(56) References Cited

FOREIGN PATENT DOCUMENTS

| WO | WO 2008/013838 | 1/2008 |
|---|---|---|
| WO | WO 2009/063244 | 5/2009 |
| WO | WO 2016/116602 | 7/2016 |
| WO | WO 2019/055966 | 3/2019 |
| WO | WO 2019/212937 | 11/2019 |
| WO | WO 2019/212946 | 11/2019 |
| WO | WO 2020/223229 | 11/2020 |
| WO | WO 2021/087018 | 5/2021 |
| WO | WO 2021/087025 | 5/2021 |

OTHER PUBLICATIONS

Belosouva et al, "DNA is a New Target of Parp3," Scientific Reports, Mar. 2018, 8:4176, 12 pages.

Bindesbøll et al., "TCDD-inducible poly-ADP-ribose polymerase (TIPARP/PARP7) mono-ADP-ribosylates and co-activates liver X receptors," Biochem, J., 2016, 473(7):899-910.

Bock "Aryl hydrocarbon receptor (AHR) functions in NAD+ metabolism, myelopoiesis and obesity", Biochemical Pharmacology 163 (2019) 128-132.

Bock, "Toward elucidation of dioxin-mediated chloracne and Ah receptor functions," Biochem. Pharmacol., 2016, 112:1-5.

Bolton et al., "Cell- and gene-specific regulation of primary target genes by the androgen receptor," Genes Dev., 2007, 21:2005-2017.

Caprara et al, "PARP14 Controls the Nuclear Accumulation of a Subset of Type I IFN-Inducible Proteins," The Journal of Immunology, Mar. 2018, 16 pages.

Cerami et al, "The cBio Cancer Genomics Portal: An Open Platform for Exploring Multidimensional Cancer Genomics Data," Cancer Discov. 2, 2012, 401-404.

Chen et al, "A macrodomain-linked immunosorbent assay (MLISA) for mono-ADPribosyltransferases," Analytical Biochemistry, 2018, 543;132-139.

Cohen & Chang, "Insights into the biogenesis, function, and regulation of ADP-ribosylation," Nat. Chem. Biol., 2018, 14:236-243.

Couturier et al., "Setting up a bioluminescence resonance energy transfer high throughput screening assay to search for protein/protein interaction inhibitors in mammalian cells," Molecular and Structural Endocrinology, 2012, 3:13 pages.

Czarnik, "Encoding strategies in combinatorial chemistry," Curr. Opin. Chem. Bio., 1997, 94(24):12378-12739.

Davis & Erlanson, "Learning from our mistakes: The 'unknown knowns' in fragment screening," Bioorganic & Medicinal Chemistry Letters, 2013, 23:2844-2852.

Diani-Moore et al, "Aryl Hydrocarbon Receptor Activation by Dioxin Targets Phosphoenolpyruvate Carboxykinase (PEPCK) for ADP-ribosylation via 2,3,7,8-Tetrachlorodibenzo-p-dioxin (TCDD)-inducible Poly(ADP-ribose) Polymerase (TiPARP)," The Journal of Biological Chemistry, 2013, 288:30:21514-21525.

Diani-Moore et al, "Identification of the Aryl Hydrocarbon Receptor Target Gene TiPARP as a Mediator of Suppression of Hepatic Gluconeogenesis by 2,3,7,8-Tetrachlorodibenzo-p-dioxin and of Nicotinamide as a Corrective Agent for This Effect," The Journal of Biological Chemistry, 2010, 285:50:38801-38810.

Dillon et al, "A FlashPlate Assay for the Identification of PARP-1 Inhibitors," Journal of Biomolecular Screening, 2003, 3(3):347-352.

Feng et al, "Role of aryl hydrocarbon receptor in cancer," Biochim. Biophys. Acta., 2013, 1836:197-210.

Ferrigno et al. "Development of substituted 6-[4-fluoro-3-(piperazin-1-ylcarbonyl)benzyl]-4,5-dimethylpyridazin-3(2H)-ones as potent poly(ADP-ribose) polymerase-1 (PARP-1) inhibitors active in BRCA deficient cells," Bioorganic & Medicinal Chemistry Letters, 2010, 20(3):1100-1105.

Gao et al., "Integrative analysis of complex cancer genomics and clinical profiles using the cBioPortal," Sci. Signal, 2013, 6:269, 19 pages.

Goode et al., "A genome-wide association study identifies susceptibility loci for ovarian cancer at 2q31 and 8q24," Nat. Genet., 2010, 42:874-879.

Gura, "Cancer Models: Systems for identifying New Drugs Are Often Faulty," Science, 1997, 278(5340):1041-1042.

Hao et al, "Xenobiotics and loss of cell adhesion drive distinct transcriptional outcomes by aryl hydrocarbon receptor signaling," Mol. Pharmacol., 2012, 82:1082-1093.

Hegde et al., "Novel PARP inhibitors sensitize human leukemic cells in an endogenous PARP activity dependent manner", RSC Advances, 2016, 6(8):6308-6319.

International Preliminary Report on Patentability in International Appln. No. PCT/US2020/030263, dated Nov. 11, 2021, 8 pages.

International Search Report & Written Opinion in International Appln. No. PCT/US2020/030263, dated Sep. 16, 2020, 24 pages.

Ji et al, "The Development of a Biotinylated NAD+-Applied Human Poly (ADP-Ribose) Polymerase 3 (PARP3) Enzymatic Assay," SLAS Discovery, Feb. 2018, 9 pages.

Johnson, et al., "Relationships between drug activity in NCI preclinical in vitro and in vivo models and early clinical trials," British Journal of Cancer, 2001, 64(10):1424-1431.

Jwa & Chang, "PARP16 is a tail-anchored endoplasmic reticulum protein required for the PERK- and IRE1-mediated unfolded protein response," Nature Cell Biology, 14(11):1223-1230.

Kim et al, "A Quantitative Assay Reveals Ligand Specificity of the DNA Scaffold Repair Protein XRCC1 and Efficient Disassembly of Complexes of XRCC1 and the Poly(ADP-ribose) Polymerase 1 by Poly(ADP-ribose) Glycohydrolase," Journal of Biological Chemistry, Dec. 2014, 290(6):3775-3783.

Kozaki et al, "Mitochondrial damage elicits a TCDD-inducible poly(ADP-ribose) polymerase-mediated antiviral response," Proc. Natl. Acad. Sci, USA, 2017, 114:2681-2686.

Lea et al, "Fluorescence polarization assays in small molecule screening," Expert Opinion on Drug Discovery, 6(1):17-32.

Leidecker et al, "Serine is a new target residue for endogenous ADP-ribosylation on histones," Nature Chemical Biology, Oct. 2016, 6 pages.

Ma "Induction and superinduction of 2, 3, 7, 8-tetrachlorodibenzop-dioxin-inducible poly(ADP-ribose) polymerase:Role of the aryl hydrocarbon receptor/aryl hydrocarbon receptor nuclear translocator transcription activation domains and a labile transcription repressor," Archives of Biochemistry and Biophysics, 2002, 404:309-316.

Ma et al, "TCDD-Inducible Poly(ADP-ribose) Polymerase: A Novel Response to 2,3,7,8- Tetrachlorodibenzo-p-dioxin," Biochemical and Biophysical Research Communications, 2001, 289:499-506.

Machleidt et al, "NanoBRET—A Novel BRET Platform for the Analysis of Protein-Protein Interactions," ACS Chemical Biology, Aug. 2015, 10(8): 1554-8929.

MacPherson et al, "2,3,7,8-Tetrachlorodibenzo-p-dioxin poly(ADP-ribose) polymerase (TIPARP, ARTD14) is a mono-ADP-ribosyltransferase and repressor of aryl hydrocarbon receptor transactivation," Nucleic Acids Res., 2013, 41:1604-1621.

MacPherson et al., "Aryl hydrocarbon receptor repressor and TIPARP (ARTD14) use similar, but also distinct mechanisms to repress aryl hydrocarbon receptor signaling," Int. J. Mol. Sci., 2014, 15:7939-7957.

Matthews, "AHR toxicity and signaling: Role of TIPARP and ADP-ribosylation," Current Opinion in Toxicology, 2017, 2:50-57.

Office Action in Japanese Appln. No. 2020-560916, dated Aug. 12, 2021, 6 pages (with English translation).

Ohmoto & Yachida, "Current status of poly(ADP-ribose) polymerase inhibitors and future directions," Onco. Targets Ther., 2017, 10:5195-5208.

Opitz et al, "An endogenous tumour-promoting ligand of the human aryl hydrocarbon receptor," Nature, 2011, 478:197-203.

Pan et al, "A major chromatin regulator determines resistance of tumor cells to T cell-mediated killing," Science, 2018, 359:770-775.

Papeo et al, "Insights into PARP Inhibitors' Selectivity Using Fluorescence Polarization and Surface Plasmon Resonance Binding Assays," Journal of Biomolecular Screening, 2014, 19(8):1212-1219.

(56) References Cited

OTHER PUBLICATIONS

PCT International Preliminary Report on Patentability in International Appln. No. PCT/US2019/029582, dated Nov. 3, 2020, 6 pages.
PCT International Preliminary Report on Patentability in International Appln. No. PCT/US2019/029599, dated Nov. 3, 2020, 7 pages.
PCT International Search Report and Written Opinion in International Appln. No. PCT/US2019/029582, dated Jun. 19, 2019, 9 pages.
PCT International Search Report and Written Opinion in International Appln. No. PCT/US2019/029599, dated Jul. 19, 2019, 11 pages.
PCT International Search Report and Written Opinion in International Appln. No. PCT/US2020/057819, dated Feb. 11, 2021, 8 pages.
PCT International Search Report and Written Opinion in International Appln. No. PCT/US2020/057831, dated Feb. 11, 2021, 8 pages.
Pearce, et al., "Failure modes in anticancer drug discovery and development," Cancer Drug Design and Discovery, Ed. Stephen Neidle, Chapter 18, 2008, pp. 424-435.
Peng et al, "Small Molecule Microarray Based Discovery of PARP14 Inhibitors," Angew. Chem. Int. Ed., 2016, 55:1-7.
Roper et al, "ADP-ribosyltransferases Parp1 and Parp7 safeguard pluripotency of ES cells," Nucleic Acids Research, 2014, 42:14:8914-8927.
Schmahl et al, "PDGF signaling specificity is mediated through multiple immediate early genes," Nat. Genet., 2007, 39:52-60.
Simone, "Oncology: Introduction," Cecil Textbook of Medicine, 20th Edition, 1996, vol. 1, pp. 1004-1010.
STN Search, conducted Mar. 23, 2018, 34 pages.
STN Search, conducted Mar. 5, 2018, 14 pages.
STN Search, conducted Mar. 5, 2018, 31 pages.
STN Search, conducted Oct. 15, 2019, 5 pages.
STN Search, conducted Oct. 15, 2019, 8 pages.
Stockinger et al., "The Aryl Hydrocarbon Receptor: Multitasking in the Immune System," Annual Review of Immunology, 2014, 32:403-432.
Thorsell et al, "Structural Basis for Potency and Promiscuity in Poly(ADP-ribose) Polymerase (PARP) and Tankyrase Inhibitors," J. Med. Chem., Dec. 2016, A-J.
Tokunaga et al, "CXCL9, CXCL10, CXCL11/CXCR3 axis for immune activation—A target for novel cancer therapy," Cancer Treatment Rev 63, 2018, 40-47.
Venkannagari et al, "Activity-based assay for human mono-ADP-ribosyltransferases ARTD7/PARP15 and ARTD10/PARP10 aimed at screening and profiling inhibitors," European Journal of Pharmaceutical Sciences, 2013, 49:148-156.
Vyas et al, "A systematic analysis of the PARP protein family identifies new functions critical for cell physiology," Nat. Commun., 2013, 4:2240, 13 pages.
Vyas et al, "New PARP targets for cancer therapy," Nat Rev Cancer, Jun. 5, 2014, 14:502-509.
Vyas et al., "Family-wide analysis of poly(ADP-ribose) polymerase activity," 2014, Nat. Commun., 5:4426, 13 pages.
Wahlberg et al, "Family-wide chemical profiling and structural analysis of PARP and tankyrase inhibitors," Nature Biotechnology, Mar. 2012, 30(3):283-288.
Yamada et al, "Constitutive aryl hydrocarbon receptor signaling constrains Type I interferon-mediated antiviral innate defense," Nat. Immunol., 2016, 17:687-694.
Ye at al. "Design, Synthesis, and Biological Evaluation of a Series of Benzo[de][1,7]naphthyridin-7(8H)-ones Bearing a Functionalized Longer Chain Appendage as Novel PARP1 Inhibitors", Journal of Medicinal Chemistry, 2013, 56(7):2885-2903.
Yoneyama-Hirozane et al, "Identification of PARP14 inhibitors using novel methods for detecting auto-ribosylation," Biochemical and Biophysical Research Communications, 2017, 1-6.
Yuen et al ,"A Focused DNA-encoded Chemical Library for the Discovery of Inhibitors of NAD+-dependent Enzymes," J. Am. Chem. Soc., Mar. 2019, 15 pages.
Zaffini et al, "Asthma and poly(ADP-ribose) polymerase inhibition: a new therapeutic approach," Drug Design, Development and Therapy, 2018, 12:281-2913.
Zitvogel et al., Type I interferons in anticancer immunity. Nat Rev Immun 15, 2015, 405.
Gamba et al., "Identification of novel 2-benzoxazolinone derivatives with specific inhibitory activity against the HIV-1 nucleocapsid protein," European Journal of Medicinal Chemistry, Feb. 2018, 145:154-164.
Schwartz et al., "Applications of tert-amino effect and a nitrone-olefin 1,3-dipolar cycloaddition reaction: synthesis of novel angularly annelated diazino heterocycles," Journal of Molecular Struture: THEOCHEM, Aug. 2000, 528(1-3):49-57.
Extended European Search Report in European Appln No. 23161423.1, mailed on Sep. 11, 2023, 5 pages.
Office Action in Australian Appln. No. 2019262927, mailed on Oct. 27, 2022, 2 pages.
Office Action in Brazilian Appln. No. 112020022006-0, mailed on Apr. 4, 2023, 5 pages (with English translation).
Office Action in Chilean Appln. No. 2020-002821, mailed on Dec. 20, 2021, 22 pages (with English translation).
Office Action in Chilean Appln. No. 2020-002821, mailed on Sep. 13, 2022, 22 pages (with English translation).
Office Action in Chinese Appln. No. 201980044076.5, mailed on Mar. 18, 2023, 15 pages (with English translation).
Office Action in Chinese Appln. No. 202080083214.3, mailed on Jul. 15, 2023, 12 pages (with English translation).
Office Action in Colombian Appln. No. NC 2020/0013599, mailed on Nov. 25, 2022, 11 pages (with English translation).
Office Action in Colombian Appln. No. NC 2020/0013599, mailed on Nov. 7, 2020, 2 pages (with English translation).
Office Action in Costa Rican Appln. No. 2020-000518, mailed on Mar. 4, 2024, 18 pages (with English translation).
Office Action in Costa Rican Appln. No. 2020-000518, mailed on Nov. 20, 2024, 18 pages (with English translation).
Office Action in Ecuadorian Appln. No. SENADI-2020-69404, mailed on Nov. 25, 2020, 2 pages (with English translation).
Office Action in Eurasian Appln. No. 202092590, mailed on Jan. 20, 2022, 6 pages (with English translation).
Office Action in Eurasian Appln. No. 202092590, mailed on Jan. 22, 2024, 8 pages (with English translation).
Office Action in Eurasian Appln. No. 202291315, mailed on Jun. 15, 2023, 6 pages (with English translation).
Office Action in Eurasian Appln. No. 202291315, mailed on Nov. 20, 2024, 2 pages (with English translation).
Office Action in European Appln. No. 19723272.1, mailed on Dec. 9, 2020, 3 pages.
Office Action in European Appln. No. 19723272.1, mailed on Sep. 20, 2021, 4 pages.
Office Action in European Appln. No. 23161423.1, mailed on Jan. 13, 2025, 4 pages.
Office Action in Indian Appln. No. 202017046239, mailed on Jul. 20, 2022, 6 pages (with English translation).
Office Action in Indian Appln. No. 202017046239, mailed on Oct. 16, 2023, 2 pages (with English translation).
Office Action in Indian Appln. No. 202217029911, mailed on Sep. 25, 2024, 6 pages (with English translation).
Office Action in Indonesian Appln. No. P00202205488, mailed on May 2, 2024, 5 pages (with English translation).
Office Action in Israeli Appln. No. 278,116, mailed on Jun. 6, 2021, 6 pages (with English translation).
Office Action in Israeli Appln. No. 278,116, mailed on Nov. 14, 2022, 3 pages (English translation only).
Office Action in Israeli Appln. No. 292,432, mailed on Dec. 26, 2024, 4 pages (with English translation).
Office Action in Israeli Appln. No. 292,432, mailed on Nov. 17, 2022, 5 pages (with English translation).
Office Action in Israeli Appln. No. 308,983, mailed on Dec. 18, 2023, 6 pages (with English translation).

(56) References Cited

OTHER PUBLICATIONS

Office Action in Israeli Appln. No. 308,983, mailed on Nov. 13, 2024, 3 pages (English translation only).
Office Action in Japanese Appln. No. 2021-145986, mailed on Feb. 13, 2024, 4 pages (with English translation).
Office Action in Japanese Appln. No. 2021-145986, mailed on Jan. 16, 2024, 5 pages (with English translation).
Office Action in Japanese Appln. No. 2021-145986, mailed on May 7, 2024, 14 pages (with English translation).
Office Action in Japanese Appln. No. 2022-525496, mailed on Sep. 17, 2024, 7 pages (with English translation).
Office Action in Korean Appln. No. 10-2020-7034323, mailed on Jul. 18, 2024, 9 pages (with English translation).
Office Action in Mexican Appln. No. MX/A/2020/011465, mailed on Oct. 18, 2022, 8 pages (with English translation).
Office Action in Peru Appln. No. 0001749-2020/DIN, mailed on Sep. 20, 2024, 14 pages (with English translation).
Office Action in Philippine Appln. No. 1-2020-551760, mailed on Dec. 2, 2024, 5 pages.
Office Action in Taiwanese Appln. No. 109137556, mailed on Jan. 9, 2025, 8 pages (with English translation).
Office Action in Taiwanese Appln. No. 108114978, mailed on Jan. 13, 2023, 25 pages (with English translation).
Office Action in Taiwanese Appln. No. 112127538, mailed on Sep. 5, 2023, 8 pages (with English translation).
Office Action in Taiwenese Appln. No. 109137556, mailed on Jul. 9, 2024, 20 pages (with English translation).
Office Action in Thai Appln. No. 2001006218, mailed on Dec. 25, 2023, 9 pages (with English translation).
Office Action in Ukrainian Appln. No. a202007549, mailed on Feb. 7, 2024, 4 pages (with English translation).
Office Action in Vietnamese Appln. No. 1-2022-03297, mailed on Jun. 25, 2024, 3 pages (with English translation).
Promega Technical Buletin, "NanoBRET™ Target Engagement Intracellular HDAC Assay," Promega Corporation, 2800 Woods Hollow Road, Madison, WI, 2016, pp. 1-24.
STN Registry No. 1252156-61-8, "CN 4-Chloro-5-[[3-(3,4-dihydro-1(2H)-quinolinyl)-3-oxopropyl]amino]-3(2H)-pyridazinone," Nov. 9, 2010, 1 page.
STN Registry No. 1375963-69-1, "CN 4-Chloro-5-[[3-[4-(3-methylphenyl)-1-piperazinyl]propyl]amino]-3(2H)-pyridazinone," Jun. 7, 2012, 1 page.
STN Registry No. 1484783-67-6, "CN 4-chloro-5-[[2-methyl-3-(1-piperidinyl)propyl]amino]-3(2H)-pyridazinone," Dec. 1, 2013, 1 page.
STN Registry No. 1485466-57-6, "CN 4-Chloro-5-[[3-(2-methyl-1-piperidinyl)propyl]amino]-3(2H)-pyridazinone," Dec. 2, 2013, 1 page.
STN Registry No. 1490079-97-4, "CN 4-Chloro-5-[[3-(1H-imidazol-1-yl)propyl]amino]-3(2H)-pyridazinone," Dec. 8, 2013, 1 page.
STN Registry No. 1495798-46-3, "CN 4-Chloro-5-[[3-(1-pyrrolidinyl)propyl]amino]-3(2H)-pyridazinone," Dec. 16, 2013, 1 page.
STN Registry No. 1510953-57-7, "CN 4-Chloro-5-[[2-methyl-3-(1-pyrrolidinyl)propyl]amino]-3(2H)-pyridazinone," Jan. 5, 2014, 1 page.
STN Registry No. 1521001-17-1, "CN 4-Chloro-5-[[4-(1H-imidazol-1-yl)butyl]amino]-3(2H)-pyridazinone," Jan. 15, 2014, 1 page.
STN Registry No. 1542530-79-9, "CN 4-Chloro-5-[[3-(1-piperazinyl)propyl]amino]-3(2H)-pyridazinone," Feb. 13, 2014, 1 page.
STN Registry No. 1707598-02-4, "CN 4-Chloro-5-[[3-(1H-pyrazol-1-yl)propyl]amino]-3(2H)-pyridazinone," May 19, 2015, 1 page.
STN Registry No. 1707983-59-2, "CN 4-Bromo-5-[[3-(4-morpholinyl)propyl]amino]-3(2H)-pyridazinone," May 19, 2015, 1 page.
STN Registry No. 1710191-97-1, "CN 4-Bromo-5-[[3-(2-methyl-1-piperidinyl)propyl]amino]-3(2H)-pyridazinone," May 22, 2015, 1 page.
STN Registry No. 1710334-93-2, "CN 4-Bromo-5-[[3-(1H-pyrazol-1-yl)propyl]amino]-3(2H)-pyridazinone," May 22, 2015, 1 page.
STN Registry No. 1710343-80-8, "CN 4-Bromo-5-[[3-oxo-3-(1-pyrrolidinyl)propyl]amino]-3(2H)-pyridazinone," May 22, 2015, 1 page.
STN Registry No. 1710349-07-7, "CN 4-Bromo-5-[[3-(4-morpholinyl)-3-oxopropyl]amino]-3(2H)-pyridazinone," May 22, 2015, 1 page.
STN Registry No. 1710531-07-9, "CN 4-Chloro-5-[[3-oxo-3-(1-pyrrolidinyl)propyl]amino]-3(2H)-pyridazinone," May 22, 2015, 1 page.
STN Registry No. 1710945-38-2, "CN 4-Bromo-5-[[3-(3,5-dimethyl-1H-pyrazol-1-yl)propyl]amino]-3(2H)-pyridazinone," May 24, 2015, 1 page.
STN Registry No. 1711796-42-7, "CN 4-Bromo-5-[[3-oxo-3-(1-piperidinyl)propyl]amino]-3(2H)-pyridazinone," May 25, 2015, 1 page.
STN Registry No. 1713221-50-1, "CN 4-Chloro-5-[[3-(4-morpholinyl)-3-oxopropyl]amino]-3(2H)-pyridazinone," May 26, 2015, 1 page.
STN Registry No. 1713222-21-9, "CN 4-Bromo-5-[[3-(1-pyrrolidinyl)propyl]amino]-3(2H)-pyridazinone," May 26, 2015, 1 page.
STN Registry No. 1770153-94-0, "CN 4-Bromo-5-[[2-methyl-3-(1-piperidinyl)propyl]amino]-3(2H)-pyridazinone," Jun. 1, 2015, 1 page.
STN Registry No. 1770154-16-9, "CN 4-Bromo-5-[[2-methyl-3-(1-pyrrolidinyl)propyl]amino]-3(2H)-pyridazinone," Jun. 1, 2015, 1 page.
STN Registry No. 1770154-34-1, "CN 4-Bromo-5-[[3-(1H-1,2,3-triazol-1-yl)propyl]amino]-3(2H)-pyridazinone," Jun. 1, 2015, 1 page.
STN Registry No. 1774932-00-1, "CN 4-Bromo-5-[[3-(1H-imidazol-1-yl)propyl]amino]-3(2H)-pyridazinone," Jun. 7, 2015, 1 page.
STN Registry No. 1774949-89-1, "CN 4-Chloro-5-[[3-(3,5-dimethyl-1H-pyrazol-1-yl)propyl]amino]-3(2H)-pyridazinone," Jun. 7, 2015, 1 page.
STN Registry No. 1775918-08-5, "CN 4-Chloro-5-[[3-oxo-3-(1-piperidinyl)propyl]amino]-3(2H)-pyridazinone," Jun. 8, 2015, 1 page.
STN Registry No. 1777885-96-7, "CN 4-Bromo-5-[[4-(1H-imidazol-1-yl)butyl]amino]-3(2H)-pyridazinone," Jun. 11, 2015, 1 page.
STN Registry No. 1797223-27-8, "CN 4-Chloro-5-[[4-(2,3-dihydro-1H-indol-1-yl)-4-oxobutyl] amino]-3(2H)-pyridazinone," Jul. 8, 2015, 1 page.
STN Registry No. 1797312-44-7, "CN 4-Chloro-5-[[4-(2,6-dimethyl-4-morpholinyl)butyl] amino]-3(2H)-pyridazinone," Jul. 8, 2015, 1 page.
STN Registry No. 1916850-83-3, "CN 4-Chloro-5-[[3-(1H-1,2,3-triazol-1-yl) propyl]amino]-3(2H)-pyridazinone," Aug. 16, 2023, 1 page.
STN Registry No. 2001824-09-3, "CN 5-[[3-(1-azetidinyl) propyl] amino]-4-bromo-3(2H)-pyridazinone," Sep. 29, 2016, 1 page.
STN Registry No. 2007011-73-4, "CN 5-[[3-(1-azetidinyl) propyl] amino]-4-chloro-3(2H)-pyridazinone," Oct. 6, 2016, 1 page.
STN Registry No. 2123847-27-6, "3(2H)-Pyridazinone, 4-chloro-5-[(3aR,7aS)-octahydro-2H-isoindol-2-yl]-,rel-," Sep. 1, 2017, 8 pages.
STN Registry No. 807665-16-3, "CN 4-Chloro-5-[[3-(4-morpholinyl)propyl]amino]-3(2H)-pyridazinone," Jan. 4, 2005, 1 page.
STN Search, conducted Mar. 16, 2023, 8 pages.
Vasta et al., "Quantitative, wide-spectrum kinase profiling in live cells for assessing the effect of cellular ATP on target engagement," Cell chemical biology, Feb. 15, 2018, 25(2):206-214, 21 pages.
Written Opinion in Singaporean Appln. No. 11202204293P, mailed on Nov. 20, 2024, 5 pages.

SOLID FORMS OF A PARP7 INHIBITOR

CROSS-REFERENCE TO RELATED APPLICATIONS

This application is a National Stage Application under 35 U.S.C. § 371 and claims the benefit of International Application No. PCT/US2020/030263, filed Apr. 28, 2020, which claims priority to International Application No. PCT/CN2019/084914, filed Apr. 29, 2019, the disclosure of which is incorporated herein by reference.

FIELD OF THE INVENTION

The present invention relates to solid forms of the poly(ADP-ribose) polymerase 7 (PARP7) inhibitor 5-[[(2S)-1-(3-oxo-3-[4-[5-(trifluoromethyl)pyrimidin-2-yl]piperazin-1-yl]propoxy)propan-2-yl]amino]-4-(trifluoromethyl)-2,3-dihydropyridazin-3-one, and salts thereof, including methods of preparation thereof, where the inhibitor is useful in the treatment of cancer.

BACKGROUND OF THE INVENTION

Poly(ADP-ribose) polymerases (PARPs) are members of a family of seventeen enzymes that regulate fundamental cellular processes including gene expression, protein degradation, and multiple cellular stress responses (M. S. Cohen, P. Chang, Insights into the biogenesis, function, and regulation of ADP-ribosylation. *Nat Chem Biol* 14, 236-243 (2018)). The ability of cancer cells to survive under stress is a fundamental cancer mechanism and an emerging approach for novel therapeutics. One member of the PARP family, PARP1, has already been shown to be an effective cancer target in connection to cellular stress induced by DNA damage, either induced by genetic mutation or with cytotoxic chemotherapy, with three approved drugs in the clinic and several others in late stage development (A. Ohmoto, S. Yachida, Current status of poly(ADP-ribose) polymerase inhibitors and future directions. *Onco Targets Ther* 10, 5195-5208 (2017)).

The seventeen members of the PARP family were identified in the human genome based on the homology within their catalytic domains (S. Vyas, M. Chesarone-Cataldo, T. Todorova, Y. H. Huang, P. Chang, A systematic analysis of the PARP protein family identifies new functions critical for cell physiology. *Nat Commun* 4, 2240 (2013)). However, their catalytic activities fall into 3 different categories (S. Vyas et al., Family-wide analysis of poly(ADP-ribose) polymerase activity. *Nat Commun* 5, 4426 (2014)). The majority of PARP family members catalyze the transfer of mono-ADP-ribose units onto their substrates (monoPARPs), while others (PARP1, PARP2, TNKS, TNKS2) catalyze the transfer of poly-ADP-ribose units onto substrates (polyPARPs). Finally, PARP13 is thus far the only PARP for which catalytic activity could not be demonstrated either in vitro or in vivo.

The aryl hydrocarbon receptor (AHR) is a ligand-activated transcription factor involved in regulating multiple cellular functions including proinflammatory responses and xenobiotic metabolism (S. Feng, Z. Cao, X. Wang, Role of aryl hydrocarbon receptor in cancer. *Biochim Biophys Acta* 1836, 197-210 (2013); and B. Stockinger, P. Di Meglio, M. Gialitakis, J. H. Duarte, The aryl hydrocarbon receptor: multitasking in the immune system. *Annu Rev Immunol* 32, 403-432 (2014)). The AHR can be activated by a broad number of ligands including endogenous tryptophan metabolites such as kynurenine (C. A. Opitz et al., An endogenous tumour-promoting ligand of the human aryl hydrocarbon receptor. *Nature* 478, 197-203 (2011)) and certain polycyclic aromatic hydrocarbons such as 2,3,7,8-tetrachlorodibenzo-p-dioxin (TCDD) (K. W. Bock, Toward elucidation of dioxin-mediated chloracne and Ah receptor functions. *Biochem Pharmacol* 112, 1-5 (2016)). Activation of the AHR induces target gene expression including genes involved in metabolism such as cytochrome P4501A1 and P4501B1. Activation of AHR also leads to an increase in the AHR target gene, TCDD-inducible poly(ADP-ribose)polymerase (TIPARP, also referred to as PARP7), which functions as a negative regulator of certain AHR transcriptional targets (L. MacPherson et al., Aryl hydrocarbon receptor repressor and TIPARP (ARTD14) use similar, but also distinct mechanisms to repress aryl hydrocarbon receptor signaling. *Int J Mol Sci* 15, 7939-7957 (2014); and L. MacPherson et al., 2,3,7,8-Tetrachlorodibenzo-p-dioxin poly(ADP-ribose) polymerase (TIPARP, ARTD14) is a mono-ADP-ribosyltransferase and repressor of aryl hydrocarbon receptor transactivation. *Nucleic Acids Res* 41, 1604-1621 (2013)).

PARP7 can also be regulated by other transcription factors and signaling pathways including androgen receptor (E. C. Bolton et al., Cell- and gene-specific regulation of primary target genes by the androgen receptor. *Genes Dev* 21, 2005-2017 (2007)), platelet derived growth factor (J. Schmahl, C. S. Raymond, P. Soriano, PDGF signaling specificity is mediated through multiple immediate early genes. *Nat Genet* 39, 52-60 (2007)) and hypoxia inducible factor 1 (N. Hao et al., Xenobiotics and loss of cell adhesion drive distinct transcriptional outcomes by aryl hydrocarbon receptor signaling. *Mol Pharmacol* 82, 1082-1093 (2012)). The PARP7 gene is located on chromosome 3 (3q25) in a region that is frequently amplified in cancers of squamous histology (cbioportal.org). A genome-wide association study identified 3q25 as susceptibility loci for ovarian cancer suggesting a role for PARP7 in this cancer type (E. L. Goode et al., A genome-wide association study identifies susceptibility loci for ovarian cancer at 2q31 and 8q24. *Nat Genet* 42, 874-879 (2010)). PARP7 has multiple cellular functions. In the context of AHR signaling PARP7 acts as a negative feedback mechanism to regulate the expression of P4501A1 and P4501B1 (L. MacPherson et al., Aryl hydrocarbon receptor repressor and TIPARP (ARTD14) use similar, but also distinct mechanisms to repress aryl hydrocarbon receptor signaling. *Int J Mol Sci* 15, 7939-7957 (2014), and L. MacPherson et al., 2,3,7,8-Tetrachlorodibenzo-p-dioxin poly(ADP-ribose) polymerase (TIPARP, ARTD14) is a mono-ADP-ribosyltransferase and repressor of aryl hydrocarbon receptor transactivation. *Nucleic Acids Res* 41, 1604-1621 (2013)). PARP7 has also been described to ADP-ribosylate liver X receptors which leads to the modulation of their transcriptional activity (C. Bindesboll et al., TCDD-inducible poly-ADP-ribose polymerase (TIPARP/PARP7) mono-ADP-ribosylates and co-activates liver X receptors. *Biochem J* 473, 899-910 (2016). During viral infection PARP7 can bind to Sindbis virus (SINV) to promote viral RNA degradation (T. Kozaki et al., Mitochondrial damage elicits a TCDD-inducible poly(ADP-ribose) polymerase-mediated antiviral response. *Proc Natl Acad Sci USA* 114, 2681-2686 (2017)). Also in the context of viral infection, AHR-induced PARP7 can interact with TBK1, a major kinase that is activated during the onset of pathogen-associated molecular pattern pathways leading to an activation of the Type I interferon response and antiviral immunity (T. Yamada et al., Constitutive aryl hydrocarbon receptor signaling constrains Type I interferon-mediated antiviral innate defense. *Nat Immunol* 17, 687-694 (2016)). PARP7 was shown to ADP-ribosylate TBK1 which prevents its activation, thereby repressing the Type I interferon response.

Based on these results from viral infection one could hypothesize that cancer cells can use aberrantly expressed and/or activated PARP7 as a mechanism to evade the host immune system through suppression of the Type I interferons and thereby T cell mediated antitumor immunity. Indeed, in a recent genetic screen to identify tumor factors that suppress T cell activation PARP7 was identified as a hit (D. Pan et al., A major chromatin regulator determines resistance of tumor cells to T cell-mediated killing. *Science* 359, 770-775 (2018)). PARP7 knockout in a mouse melanoma cell line was shown to increase the proliferation and activation of co-cultured T cells suggesting that PARP7 inhibition may be a viable strategy to activate T cell mediated tumor killing. Accordingly, there is a need for new solid forms of PARP7-inhibiting molecules for preparing pharmaceutically useful formulations and dosage forms with suitable properties related to, for example, facilitating the manufacture of safe, effective, and high quality drug products.

SUMMARY OF THE INVENTION

The present invention is directed to solid forms of 5-[[(2S)-1-(3-oxo-3-[4-[5-(trifluoromethyl)pyrimidin-2-yl]piperazin-1-yl]propoxy)propan-2-yl]amino]-4-(trifluoromethyl)-2,3-dihydropyridazin-3-one and salts thereof.

The present invention is further directed to solid forms of the free base of 5-[[(2S)-1-(3-oxo-3-[4-[5-(trifluoromethyl)pyrimidin-2-yl]piperazin-1-yl]propoxy)propan-2-yl]amino]-4-(trifluoromethyl)-2,3-dihydropyridazin-3-one.

The present invention is further directed to the benzenesulfonic acid salt of 5-[[(2S)-1-(3-oxo-3-[4-[5-(trifluoromethyl)pyrimidin-2-yl]piperazin-1-yl]propoxy)propan-2-yl]amino]-4-(trifluoromethyl)-2,3-dihydropyridazin-3-one.

The present invention is further directed to crystalline forms of the solid forms described herein.

The present invention is further directed to pharmaceutical compositions comprising a solid form described herein, and at least one pharmaceutically acceptable carrier.

The present invention is further directed to therapeutic methods of using the solid forms described herein. The present disclosure also provides uses of the solid forms described herein in the manufacture of a medicament for use in therapy. The present disclosure also provides the solid forms described herein for use in therapy.

The present invention is further directed to processes for preparing the solid forms described herein.

DETAILED DESCRIPTION

Figure 1:
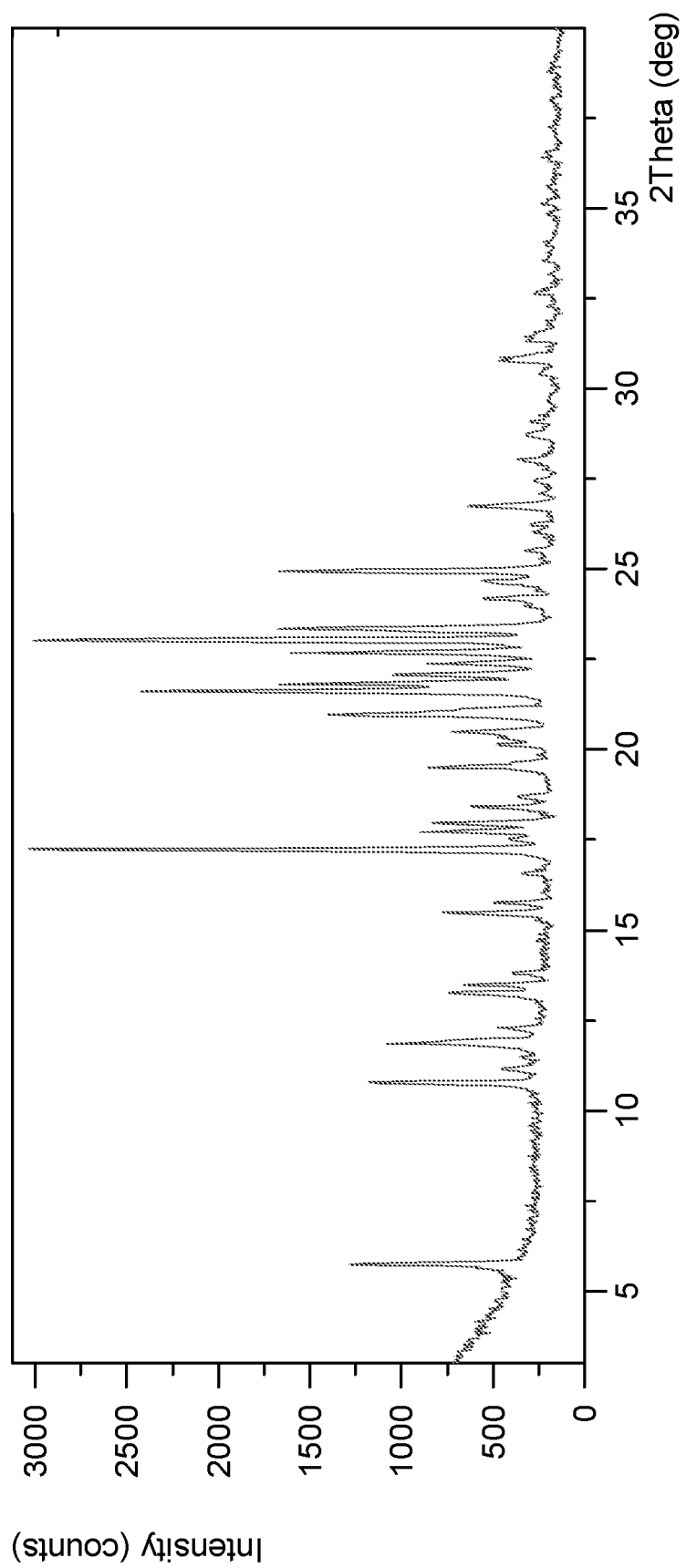
FIG. 1 shows the XRPD pattern of Form A.

The present invention is directed to, inter alia, solid forms of 5-[[(2S)-1-(3-oxo-3-[4-[5-(trifluoromethyl)pyrimidin-2-yl]piperazin-1-yl]propoxy)propan-2-yl]amino]-4-(trifluoromethyl)-2,3-dihydropyridazin-3-one (Compound 1), the structure of which is shown below.

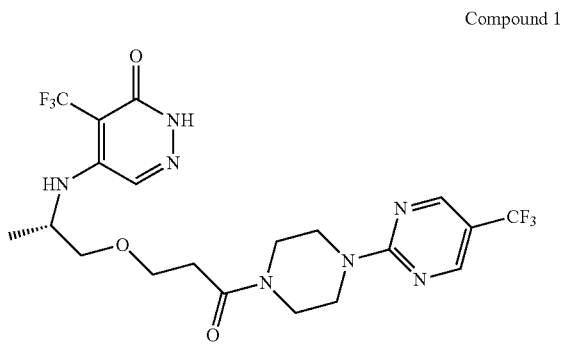 [SMILES: C[C@@H](COCCC(=O)N1CCN(c2ncc(C(F)(F)F)cn2)CC1)Nc1cn[nH]c(=O)c1C(F)(F)F]

Compound 1

Also provided herein are salts of Compound 1, and solid forms thereof.

Compound 1 can also be referred to as:
(S)-5-((1-(3-Oxo-3-(4-(5-(trifluoromethyl)pyrimidin-2-yl)piperazin-1-yl)propoxy)propan-2-yl)amino)-4-(trifluoromethyl)pyridazin-3(2H)-one; or
(S)-5-(1-(3-Oxo-3-(4-(5-(trifluoromethyl)pyrimidin-2-yl)piperazin-1-yl)propoxy)propan-2-ylamino)-4-(trifluoromethyl)pyridazin-3(2H)-one.

Compound 1 and its salts can be isolated as one or more solid forms. The solid forms (including, e.g., crystalline forms) described herein have many advantages, for example they have desirable properties, such as ease of handling, ease of processing, storage stability, and ease of purification. Moreover, the crystalline forms can be useful for improving the performance characteristics of a pharmaceutical product such as dissolution profile, shelf-life and bioavailability.

Compound 1 can be prepared in various crystalline forms including, e.g., Form A, Form B, or Form C. In some embodiments, the solid form of Compound 1 is amorphous.

In some embodiments, the salt of Compound 1 is an acid salt of Compound 1. In some embodiments, the acid forming the acid salt is benzenesulfonic acid.

In some embodiments, the salt of the invention is a benzenesulfonic acid salt of Compound 1. The benzenesulfonic acid salt form of Compound 1 is referred to herein as "Compound 1 benzenesulfonic acid salt," "Compound 1 benzenesulfonic acid," or "Compound 1 Besylate." An alternative name for the salt is 5-[[(2S)-1-(3-oxo-3-[4-[5-(trifluoromethyl)pyrimidin-2-yl]piperazin-1-yl]propoxy)propan-2-yl]amino]-4-(trifluoromethyl)-2,3-dihydropyridazin-3-one besylate. Compound 1 Besylate can be crystalline.

As used herein, the phrase "solid form" refers to a compound provided herein in either an amorphous state or a crystalline state ("crystalline form" or "crystalline solid" or "crystalline solid form"), whereby a compound provided herein in a crystalline state may optionally include solvent or water within the crystalline lattice, for example, to form a solvated or hydrated crystalline form. In some embodiments, the compound provided herein is in a crystalline state as described herein.

As used herein, the term "peak" or "characteristic peak" refers to an XRPD reflection having a relative height/intensity of at least about 3% of the maximum peak height/intensity.

As used herein, the term "crystalline" or "crystalline form" refers to a crystalline solid form of a chemical compound, including, but not limited to, a single-component or multiple-component crystal form, e.g., including solvates, hydrates, clathrates, and a co-crystal. For example, crystalline means having a regularly repeating and/or ordered arrangement of molecules, and possessing a distinguishable crystal lattice. The term "crystalline form" is meant to refer to a certain lattice configuration of a crystalline substance. Different crystalline forms of the same substance typically have different crystalline lattices (e.g., unit cells), typically have different physical properties attributed to their different crystalline lattices, and in some instances, have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify the crystalline form as well as help determine stability and solvent/water content.

Different crystalline forms of a particular substance, such as Compound 1 as described herein, can include both anhydrous forms of that substance and solvated/hydrated forms of that substance, where each of the anhydrous forms and solvated/hydrated forms are distinguished from each other by different XRPD patterns, or other solid state characterization methods, thereby signifying different crystalline lattices. In some instances, a single crystalline form (e.g., identified by a unique XRPD pattern) can have variable water or solvent content, where the lattice remains substantially unchanged (as does the XRPD pattern) despite the compositional variation with respect to water and/or solvent.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters used, the sample mounting procedure, and the particular instrument employed. In some instances, new peaks may be observed or existing peaks may disappear, depending on the type of the machine or the settings (for example, whether a Ni filter is used or not). As used herein, the term "peak" refers to a reflection having a relative height/intensity of at least about 3% or at least about 4% of the maximum peak height/intensity. Moreover, instrument variation and other factors can affect the 2-theta values. Thus, peak assignments, such as those reported herein, can vary by plus or minus about 0.2° (2-theta) and the term "substantially" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures is understood to accommodate such variation.

Crystalline forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, exposure to moisture, grinding and solvent-drop grinding.

As used herein, the term "amorphous" or "amorphous form" is intended to mean that the substance, component, or product in question is not crystalline as determined, for instance, by XRPD or where the substance, component, or product in question, for example is not birefringent when viewed microscopically. For example, amorphous means essentially without regularly repeating arrangement of molecules or lacks the long range order of a crystal, i.e., amorphous form is non-crystalline. An amorphous form does not display a defined x-ray diffraction pattern with sharp maxima. In certain embodiments, a sample comprising an amorphous form of a substance may be substantially free of other amorphous forms and/or crystalline forms. For example, an amorphous substance can be identified by an XRPD spectrum having an absence of reflections.

As used herein, the term "substantially amorphous" means a majority of the weight of a sample or preparation of Compound 1 is amorphous and the remainder of the sample is a crystalline form of the same compound. In some embodiments, a substantially amorphous sample has less than about 5% crystallinity (e.g., about 95% of the non-crystalline form of the same compound), less than about 4% crystallinity (e.g., about 96% of the non-crystalline form of the same compound), less than about 3% crystallinity (e.g., about 97% of the non-crystalline form of the same compound), less than about 2% crystallinity (e.g., about 98% of the non-crystalline form of the same compound), less than about 1% crystallinity (e.g., about 99% of the non-crystalline form of the same compound), or about 0% crystallinity (e.g., about 100% of the non-crystalline form of the same compound). In some embodiments, the term "fully amorphous" means less than about 99% or about 0% crystallinity.

Compound 1 can be prepared in batches referred to as batches, samples, or preparations. The batches, samples, or preparations can include Compound 1 in any of the crystalline or non-crystalline forms described herein, including hydrated and non-hydrated forms, and mixtures thereof.

Compounds provided herein (e.g., Compound 1) can also include all isotopes of atoms occurring in the intermediates or final compounds. Isotopes include those atoms having the same atomic number but different mass numbers. For example, isotopes of hydrogen include tritium and deuterium. One or more constituent atoms of the compounds provided herein can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7 or 8 deuterium atoms. Synthetic methods for including isotopes into organic compounds are known in the art.

In some embodiments, Compound 1 is substantially isolated. The term "substantially isolated" is meant that the compound is at least partially or substantially separated from the environment in which it was formed or detected. Partial separation can include, e.g., a composition enriched in the compound, salts, hydrates, solvates, or solid forms provided herein. Substantial separation can include compositions containing at least about 50%, at least about 60%, at least about 70%, at least about 80%, at least about 90%, at least about 95%, at least about 97%, or at least about 99% by weight of the compound, salts, hydrates, solvates, or solid forms provided herein.

The term "hydrate," as used herein, is meant to refer to a solid form of Compound 1 that includes water. The water in a hydrate can be present in a stoichiometric amount with respect to the amount of salt in the solid, or can be present in varying amounts, such as can be found in connection with channel hydrates.

As used herein, the term "substantially" when referring to a characteristic figure of a crystal form, such as an XRPD pattern, a DSC thermogram, a TGA thermogram, or the like, means that a subject figure may be non-identical to the reference depicted herein, but it falls within the limits of experimental error and thus may be deemed as derived from the same crystal form as disclosed herein, as judged by a person of ordinary skill in the art.

As used herein, the term "substantially crystalline," means a majority of the weight of a sample or preparation of Compound 1 is crystalline and the remainder of the sample is a non-crystalline form (e.g., amorphous form) of the same compound. In some embodiments, a substantially crystalline sample has at least about 95% crystallinity (e.g., about 5% of the non-crystalline form of the same compound), at least about 96% crystallinity (e.g., about 4% of the non-crystalline form of the same compound), at least about 97% crystallinity (e.g., about 3% of the non-crystalline form of the same compound), at least about 98% crystallinity (e.g., about 2% of the non-crystalline form of the same compound), at least about 99% crystallinity (e.g., about 1% of the non-crystalline form of the same compound), or about 100% crystallinity (e.g., about 0% of the non-crystalline form of the same compound). In some embodiments, the term "fully crystalline" means at least about 99% or about 100% crystallinity.

As used herein, the term "% crystallinity" or "crystalline purity," means percentage of a crystalline form in a preparation or sample which may contain other forms such as an amorphous form of the same compound, or at least one other crystalline form of the compound, or mixtures thereof. In some embodiments, the crystalline forms can be isolated with a purity of at least about 80%, about 85%, about 90%, about 95%, about 96%, about 97%, about 98%, or about 99%. In some embodiments, the crystalline forms can be isolated with a purity greater than about 99%.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "melting point" refers to an endothermic event or endothermal event observed in e.g., a DSC experiment. An endothermic event is a process or reaction in which a sample absorbs energy from its surrounding in the form of e.g., heat as in a DSC experiment. An exothermic event is a process or reaction in which a sample releases energy. The process of heat absorption and release can be detected by DSC. In some embodiments, the term "melting point" is used to describe the major endothermic event revealed on a particular DSC thermogram.

The term "room temperature" as used herein, is understood in the art, and refers generally to a temperature, e.g., a reaction temperature, that is about the temperature of the room in which the reaction is carried out, for example, a temperature from about 20° C. to about 30° C.

The term "elevated temperature" as used herein, is understood in the art, and refer generally to a temperature, e.g., a reaction temperature, that is above room temperature, e.g., above 30° C.

Compound 1 Form A

In some embodiments, Compound 1 is crystalline and has the characteristics of Form A described below.

In some embodiments, Form A has characteristic XRPD peaks at about 5.8, about 10.8, about 11.9, and about 17.2 degrees 2-theta. In some embodiments, Form A has at least one characteristic XRPD peak selected from about 5.8, about 10.8, about 11.9, and about 17.2 degrees 2-theta. In some embodiments, Form A has at least two characteristic XRPD peaks selected from about 5.8, about 10.8, about 11.9, and about 17.2 degrees 2-theta. In some embodiments, Form A has a characteristic XRPD peak at about 5.8 degrees 2-theta. In some embodiments, Form A has a characteristic XRPD peak at about 10.8 degrees 2-theta. In some embodiments, Form A has a characteristic XRPD peak at about 11.9 degrees 2-theta. In some embodiments, Form A has a characteristic XRPD peak at about 17.2 degrees 2-theta.

In some embodiments, Form A has at least one characteristic XRPD peak selected from about 5.8, about 10.8, about 11.9, about 13.3, about 13.5, about 15.5, and about 17.2 degrees 2-theta. In some embodiments, Form A has at least one characteristic XRPD peak selected from about 5.8, about 10.8, about 11.2, about 11.9, about 12.3, about 13.3, about 13.5, about 15.5, about 17.2, about 17.7, about 18.0, about 18.4, about 19.5, about 21.0, and about 21.6 degrees 2-theta.

In some embodiments, Form A has at least two characteristic XRPD peaks selected from about 5.8, about 10.8, about 11.9, about 13.3, about 13.5, about 15.5, and about 17.2 degrees 2-theta. In some embodiments, Form A has at least two characteristic XRPD peaks selected from about 5.8, about 10.8, about 11.2, about 11.9, about 12.3, about 13.3, about 13.5, about 15.5, about 17.2, about 17.7, about 18.0, about 18.4, about 19.5, about 21.0, and about 21.6 degrees 2-theta.

In some embodiments, Form A has at least three characteristic XRPD peaks selected from about 5.8, about 10.8, about 11.9, about 13.3, about 13.5, about 15.5, and about 17.2 degrees 2-theta. In some embodiments, Form A has at least three characteristic XRPD peaks selected from about 5.8, about 10.8, about 11.2, about 11.9, about 12.3, about 13.3, about 13.5, about 15.5, about 17.2, about 17.7, about 18.0, about 18.4, about 19.5, about 21.0, and about 21.6 degrees 2-theta.

In some embodiments, Form A has at least four characteristic XRPD peaks selected from about 5.8, about 10.8, about 11.9, about 13.3, about 13.5, about 15.5, and about 17.2 degrees 2-theta. In some embodiments, Form A has at least four characteristic XRPD peaks selected from about 5.8, about 10.8, about 11.2, about 11.9, about 12.3, about 13.3, about 13.5, about 15.5, about 17.2, about 17.7, about 18.0, about 18.4, about 19.5, about 21.0, and about 21.6 degrees 2-theta.

In some embodiments, Form A has an XRPD pattern with characteristic peaks as substantially shown in FIG. 1.

Figure 2:
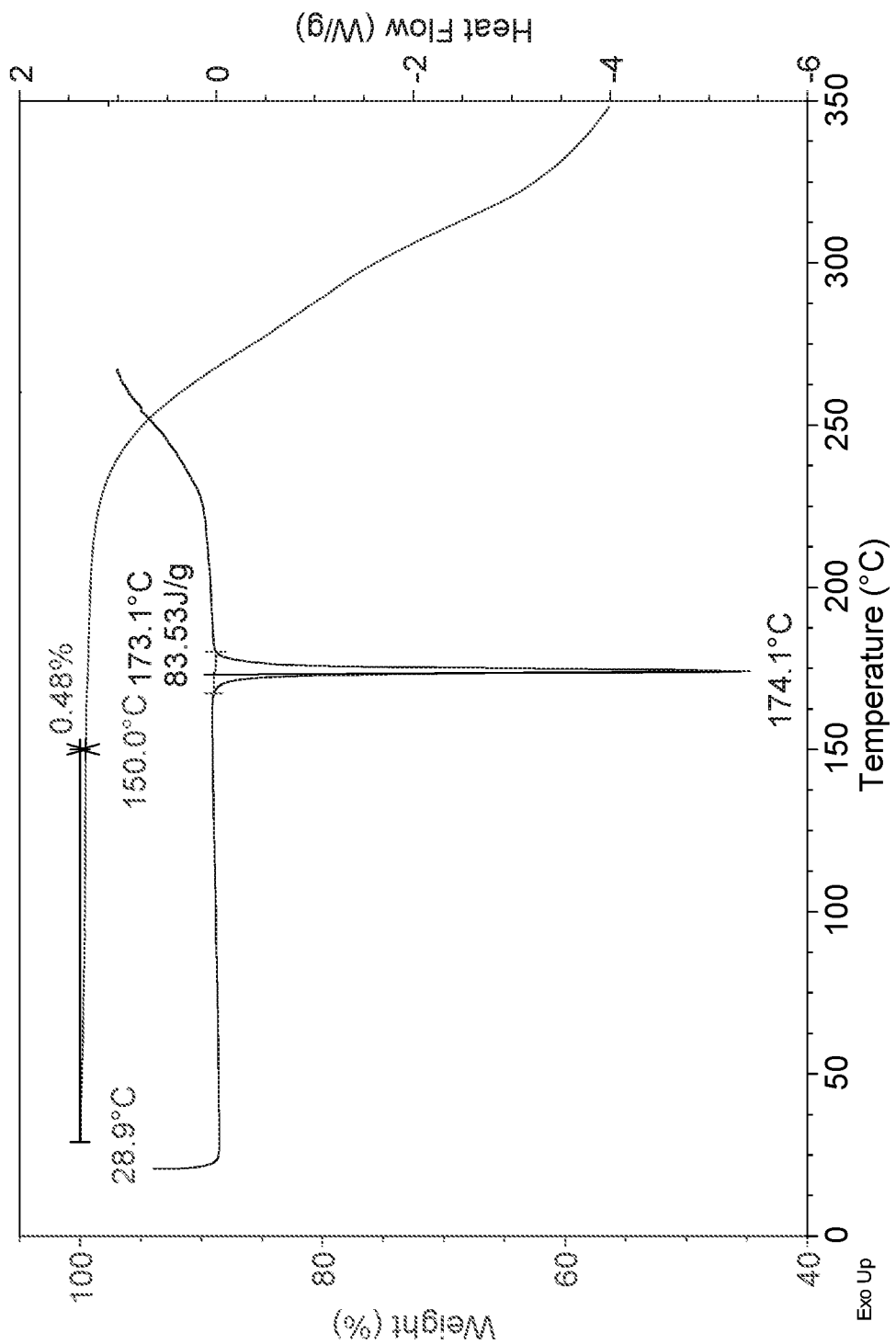
FIG. 2 shows the DSC and TGA thermogram of Form A.
Figure 3:
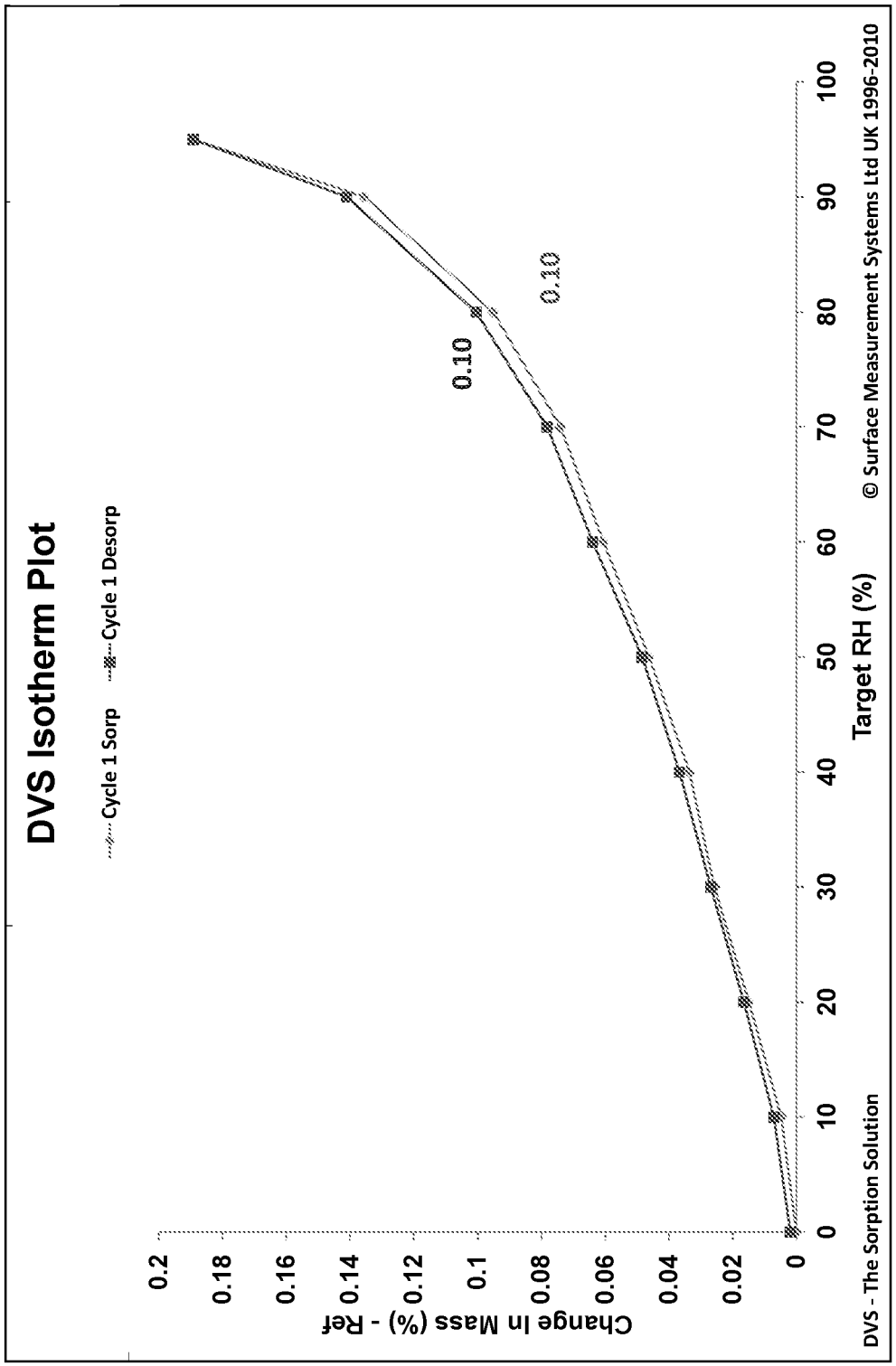
FIG. 3 shows the DVS isotherm of Form A.

In some embodiments, Form A has a DSC thermogram comprising an endotherm peak at a temperature of about 174° C. In some embodiments, Form A shows a weight loss of about 0.5% when heated to about 150° C. In some embodiments, Form A has a DSC thermogram substantially as depicted in FIG. 2. In some embodiments, Form A has a TGA thermogram substantially as depicted in FIG. 2. In some embodiments, Form A has a DVS isotherm substantially as depicted in FIG. 3.

In some embodiments, Form A has at least one characteristic XRPD peak selected from about 5.8, about 10.8, about 11.9, and about 17.2 degrees 2-theta; and has a DSC thermogram comprising an endotherm peak at a temperature of about 174° C. In some embodiments, Form A has at least one characteristic XRPD peak selected from about 5.8, about 10.8, about 11.9, and about 17.2 degrees 2-theta; and a DSC thermogram substantially as depicted in FIG. 2. In some embodiments, Form A has at least one characteristic XRPD peak selected from about 5.8, about 10.8, about 11.9, and about 17.2 degrees 2-theta; and a DVS isotherm substantially as depicted in FIG. 3.

In some embodiments, Form A can be isolated with a crystalline purity of at least about 80%, about 85%, about 90%, about 95%, about 96%, about 97%, about 98%, or about 99%. In some embodiments, Form A can be isolated with a crystalline purity greater than about 99%. In some embodiments, Form A can be isolated with a crystalline purity greater than about 99.9%. In some embodiments, Form A is substantially free of other crystalline form. In some embodiments, Form A is substantially free of amorphous form.

In some embodiments, Form A is prepared by precipitating Compound 1 from a solution comprising Compound and S1, wherein S1 is a solvent. In some embodiments, the precipitating is carried out by concentration of the solution, evaporation of S1, reduction of temperature of the solution, addition of anti-solvent, or combination thereof. In some embodiments, S1 is an organic solvent. In some embodiments, S1 is selected from one of the following solvents: ethyl alcohol, methyl isobutyl ketone, isopropyl acetate, methy t-butyl ether, 2-methyltetrahydrofuran, 1,4-dioxane, toluene, acetone, dichloromethane, dimethyl acetate, acetonitrile, ethyl acetate, isopropyl alcohol, THF, n-heptane and water. In some embodiments, the precipitating is carried out by the addition of an anti-solvent. In some embodiments, the anti-solvent is isopropyl acetate, n-heptane, methyl tert-butyl ether, ethanol, water, toluene, isopropyl alcohol, or methyl isobutyl ketone.

In some embodiments, S1 is a mixture of organic solvents. In some embodiments, S1 is a mixture of acetonitrile and n-heptane. In some embodiments, S1 is a mixture of isopropyl alcohol and ethyl acetate. In some embodiments, S1 is a mixture of chloroform and ethyl acetate. In some embodiments, S1 is a mixture of 1,4-dioxane and methanol. In some embodiments, S1 is a mixture of NMP and toluene. In some embodiments, S1 is a mixture of petroleum ether and hexanes. In some embodiments, S1 is a mixture of acetone and isopropyl alcohol. In some embodiments, S1 is a mixture of dichloromethane and methyl isobutyl ketone. In some embodiments, S1 is a mixture of chloroform and isopropyl acetate.

In some embodiments, S1 is a mixture of acetonitrile and methyl isobutyl ketone. In some embodiments, S1 is a mixture of ethyl alcohol and water. In some embodiments, S1 is a mixture of dichloromethane and methyl tert-butyl ether. In some embodiments, S1 is a mixture of 1,4-dioxane and 2-methyltetrahydrofuran. In some embodiments, S1 is a mixture of NMP and tetrahydrofuran. In some embodiments, S1 is a mixture of acetone and n-heptane. In some embodiments, S1 is a mixture of dimethyl acetate and water. In some embodiments, S1 is a mixture of acetonitrile and ethyl acetate.

In some embodiments, the precipitating is carried out in the presence of a polymer. In some embodiments, the polymer is a 1:1:1:1:1:1 mixture of polyvinyl pyrrolidone (PVP), polyvinyl alcohol (PVA), polyvinylchloride (PVC), polyvinyl acetate (PVAC), hypromellose (HPMC), and methyl cellulose (MC). In some embodiments, the polymer is 1:1:1:1:1 mixture of poly caprolactone (PCL), polyethylene glycol (PEG), polymethyl methacrylate (PMMA) sodium alginate (SA), and hydroxyethyl cellulose (HEC).

Compound 1 Form B

In some embodiments, Compound 1 is crystalline and has the characteristics of Form B described below.

In some embodiments, Form B has characteristic XRPD peaks at about 5.7, about 11.3, about 14.1, and about 16.9 degrees 2-theta. In some embodiments, Form B has at least one characteristic XRPD peak selected from about 5.7, about 11.3, about 14.1, and about 16.9 degrees 2-theta. In some embodiments, Form B has at least two characteristic XRPD peaks selected from about 5.7, about 11.3, about 14.1, and about 16.9 degrees 2-theta. In some embodiments, Form B has a characteristic XRPD peak at about 5.7 degrees 2-theta. In some embodiments, Form B has a characteristic XRPD peak at about 11.3 degrees 2-theta. In some embodiments, Form B has a characteristic XRPD peak at about 14.1 degrees 2-theta. In some embodiments, Form B has a characteristic XRPD peak at about 16.9 degrees 2-theta.

In some embodiments, Form B has at least one characteristic XRPD peak selected from about 5.7, about 11.3, about 14.1, about 16.9, about 19.8, about 25.5, and about 28.4 degrees 2-theta. In some embodiments, Form B has at least two characteristic XRPD peaks selected from about 5.7, about 11.3, about 14.1, about 16.9, about 19.8, about 25.5, and about 28.4 degrees 2-theta. In some embodiments, Form B has at least three characteristic XRPD peaks selected from about 5.7, about 11.3, about 14.1, about 16.9, about 19.8, about 25.5, and about 28.4 degrees 2-theta. In some embodiments, Form B has at least four characteristic XRPD peaks selected from about 5.7, about 11.3, about 14.1, about 16.9, about 19.8, about 25.5, and about 28.4 degrees 2-theta.

Figure 4:
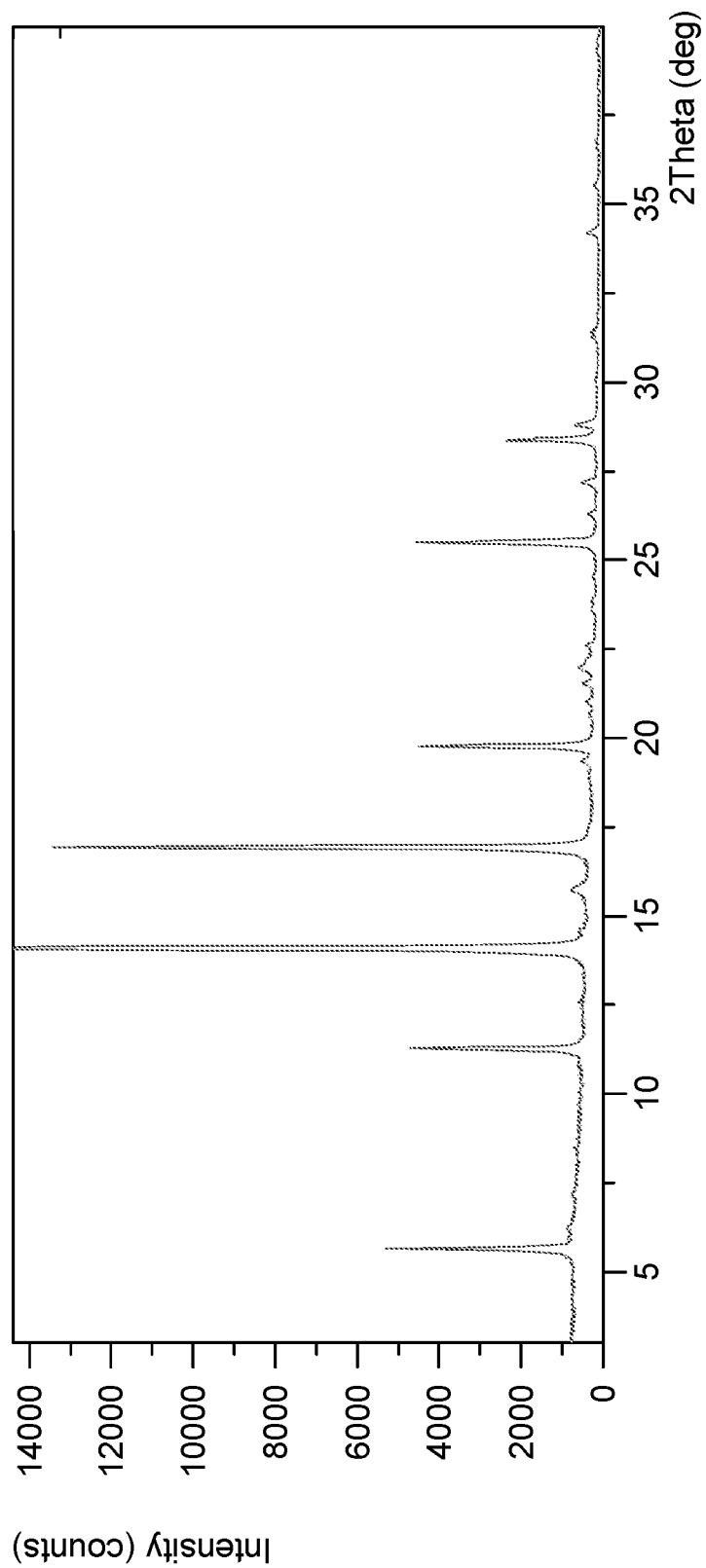
FIG. 4 shows the XRPD pattern of Form B.

In some embodiments, Form B has an XRPD pattern with characteristic peaks as substantially shown in FIG. 4.

In some embodiments, Form B has a DSC thermogram comprising endotherm peaks at temperatures of about 71° C., about 83° C., about 100° C., and about 172° C. In some embodiments, Form B has a DSC thermogram comprising an endotherm peak at a temperature of about 71° C. In some embodiments, Form B has a DSC thermogram comprising an endotherm peak at a temperature of about 83° C. In some embodiments, Form B has a DSC thermogram comprising an endotherm peak at a temperature of about 100° C. In some embodiments, Form B has a DSC thermogram comprising an endotherm peak at a temperature of about 172° C.

Figure 5:
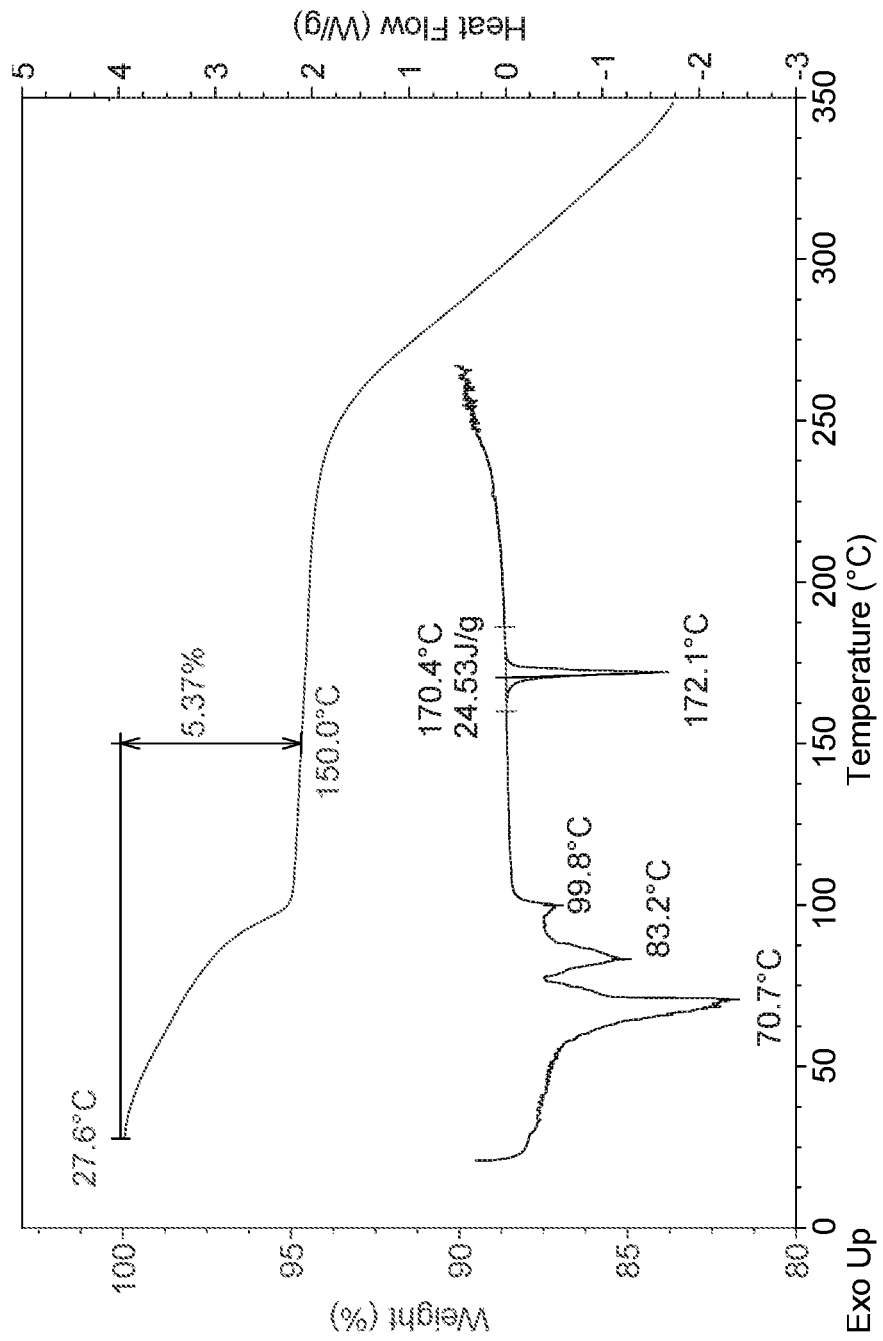
FIG. 5 shows the DSC and TGA thermogram of Form B.

In some embodiments, Form B shows a weight loss of about 5.4% when heated to about 150° C. In some embodiments, Form B has a DSC thermogram substantially as depicted in FIG. 5. In some embodiments, Form B has a TGA thermogram substantially as depicted in FIG. 5.

In some embodiments, Form B has at least one characteristic XRPD peak selected from about 5.7, about 11.3, about 14.1, and about 16.9 degrees 2-theta; and has a DSC thermogram comprising an endotherm peak at a temperature of about 71° C. In some embodiments, Form B has at least one characteristic XRPD peak selected from about 5.7, about 11.3, about 14.1, and about 16.9 degrees 2-theta; and has a DSC thermogram comprising an endotherm peak at a temperature of about 83° C. In some embodiments, Form B has at least one characteristic XRPD peak selected from about 5.7, about 11.3, about 14.1, and about 16.9 degrees 2-theta; and has a DSC thermogram comprising an endotherm peak at a temperature of about 100° C. In some embodiments, Form B has at least one characteristic XRPD peak selected from about 5.7, about 11.3, about 14.1, and about 16.9 degrees 2-theta; and has a DSC thermogram comprising an endotherm peak at a temperature of about 172° C. In some embodiments, Form B has at least one characteristic XRPD peak selected from about 5.7, about 11.3, about 14.1, and about 16.9 degrees 2-theta; and a DSC thermogram substantially as depicted in FIG. 5.

In some embodiments, Form B can be isolated with a crystalline purity of at least about 80%, about 85%, about 90%, about 95%, about 96%, about 97%, about 98%, or about 99%. In some embodiments, Form B can be isolated with a crystalline purity greater than about 99%. In some embodiments, Form B can be isolated with a crystalline purity greater than about 99.9%. In some embodiments, Form B is substantially free of other crystalline form. In some embodiments, Form B is substantially free of amorphous form.

In some embodiments, Form B is prepared by precipitating Compound 1 from a solution comprising the compound and S1, wherein S1 is a solvent. In some embodiments, the precipitating is carried out by concentration of the solution, evaporation of solvent, reduction of temperature of the solution, addition of anti-solvent, or combination thereof. In some embodiments, S1 is an organic solvent. In some embodiments, the precipitating is carried out by evaporation of S1. In some embodiments, S1 is chloroform. In some embodiments, the precipitating is carried out by addition of an anti-solvent to a solution of Compound 1 in S1. In some embodiments, S1 is chloroform. In some embodiments, the anti-solvent is n-heptane.

Compound 1 Form C

In some embodiments, Compound 1 is crystalline and has the characteristics of Form C described below.

In some embodiments, Form C has characteristic XRPD peaks at about 16.6, about 18.8, and about 21.6 degrees 2-theta. In some embodiments, Form C has at least one characteristic XRPD peak selected from about 16.6, about 18.8, and about 21.6 degrees 2-theta. In some embodiments, Form C has at least two characteristic XRPD peaks selected from about 16.6, about 18.8, and about 21.6 degrees 2-theta. In some embodiments, Form C has a characteristic XRPD peak at about 16.6 degrees 2-theta. In some embodiments, Form C has a characteristic XRPD peak at about 18.8 degrees 2-theta. In some embodiments, Form C has a characteristic XRPD peak at about 21.6 degrees 2-theta.

In some embodiments, Form C has at least one characteristic XRPD peak selected from about 16.6, about 18.8, about 21.6, about 22.3, and about 24.9 degrees 2-theta. In some embodiments, Form C has at least two characteristic XRPD peaks selected from about 16.6, about 18.8, about 21.6, about 22.3, and about 24.9 degrees 2-theta. In some embodiments, Form C has at least three characteristic XRPD peaks selected from about 16.6, about 18.8, about 21.6, about 22.3, and about 24.9 degrees 2-theta. In some embodiments, Form C has at least four characteristic XRPD peaks selected from about 16.6, about 18.8, about 21.6, about 22.3, and about 24.9 degrees 2-theta.

Figure 6:
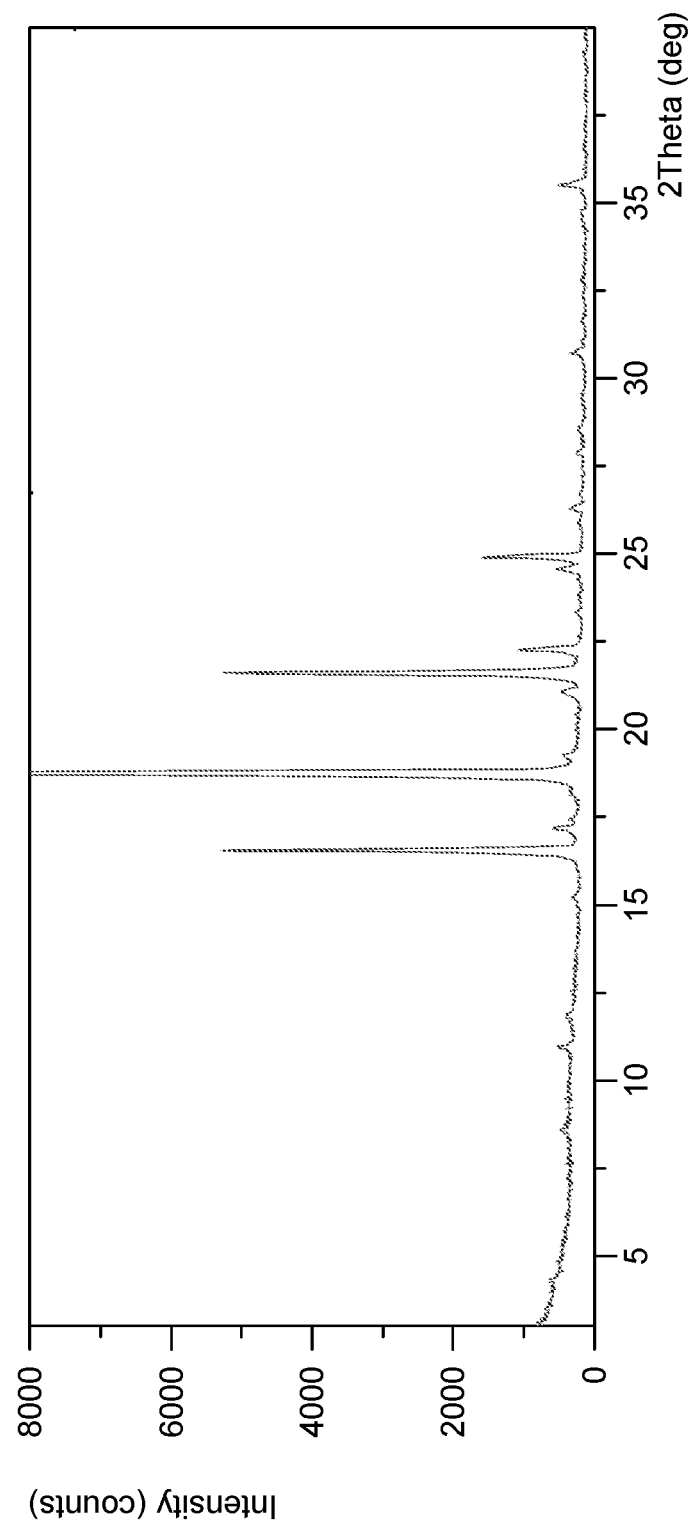
FIG. 6 shows the XRPD pattern of Form C.

In some embodiments, Form C has an XRPD pattern with characteristic peaks as substantially shown in FIG. 6.

Figure 7:
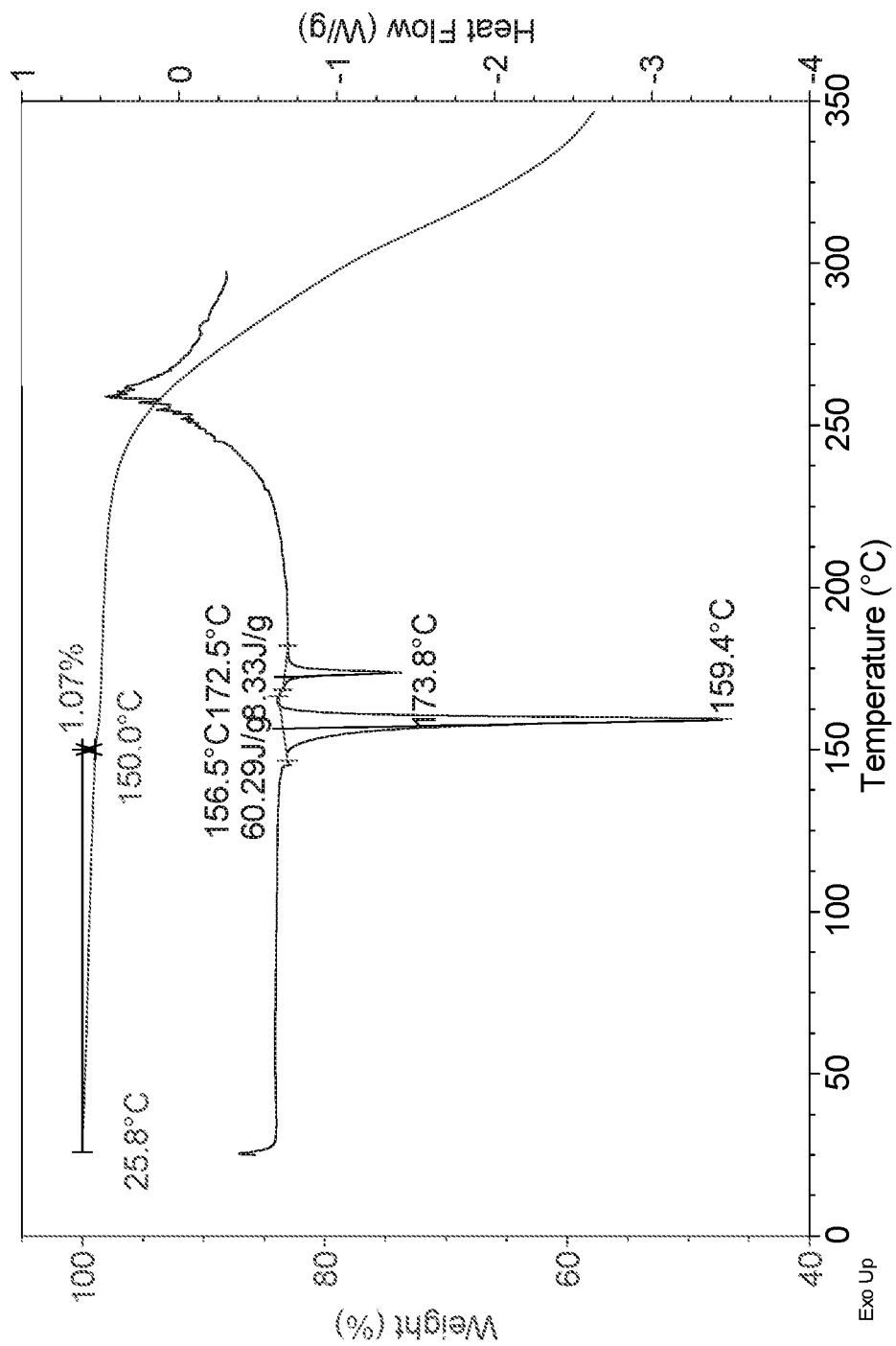
FIG. 7 shows the DSC and TGA thermogram of Form C.

In some embodiments, Form C has a DSC thermogram comprising endotherm peaks at temperatures of about 159° C. and about 174° C. In some embodiments, Form C has a DSC thermogram comprising an endotherm peak at a temperature of about 159° C. In some embodiments, Form C has a DSC thermogram comprising an endotherm peak at a temperature of about 174° C. In some embodiments, Form C shows a weight loss of about 1.1% when heated to about 150° C. In some embodiments, Form C has a DSC thermogram substantially as depicted in FIG. 7. In some embodiments, Form C has a TGA thermogram substantially as depicted in FIG. 7.

In some embodiments, Form C has at least one characteristic XRPD peak selected from about 16.6, about 18.8, and about 21.6 degrees 2-theta; and has a DSC thermogram comprising an endotherm peak at a temperature of about 159° C. In some embodiments, Form C has at least one characteristic XRPD peak selected from about 16.6, about 18.8, and about 21.6 degrees 2-theta; and has a DSC thermogram comprising an endotherm peak at a temperature of about 174° C. In some embodiments, Form C has at least one characteristic XRPD peak selected from about 16.6, about 18.8, and about 21.6 degrees 2-theta; and a DSC thermogram substantially as depicted in FIG. 7.

In some embodiments, Form C can be isolated with a crystalline purity of at least about 80%, about 85%, about 90%, about 95%, about 96%, about 97%, about 98%, or about 99%. In some embodiments, Form C can be isolated with a crystalline purity greater than about 99%. In some embodiments, Form C can be isolated with a crystalline purity greater than about 99.9%. In some embodiments, Form C is substantially free of other crystalline form. In some embodiments, Form C is substantially free of amorphous form.

In some embodiments, Form C is prepared by precipitating Compound 1 from a solution comprising the compound and S1, wherein S1 is a solvent. In some embodiments, the precipitating is carried out by concentration of the solution, evaporation of solvent, reduction of temperature of the solution, addition of anti-solvent, or combination thereof. In some embodiments, S1 is an organic solvent. In some embodiments, the precipitating is carried out by evaporation of S1. In some embodiments, S1 is a mixture of acetonitrile and water, a mixture of dichloromethane and methyl tert-butyl ether, or a mixture of acetonitrile and tetrahydrofuran.

In some embodiments, the precipitating is carried out by addition of an anti-solvent to a solution of Compound 1 in S1. In some embodiments, S1 is acetone, dichloromethane, or acetonitrile. In some embodiments, the anti-solvent is 2-methyltetrahydrofuran or tetrahydrofuran.

In some embodiments, the precipitating is carried out in the presence of a polymer. In some embodiments, the polymer is a 1:1:1:1:1:1 mixture of polyvinyl pyrrolidone (PVP), polyvinyl alcohol (PVA), polyvinylchloride (PVC), polyvinyl acetate (PVAC), hypromellose (HPMC), and methyl cellulose (MC). In some embodiments, the polymer is 1:1:1:1:1 mixture of polycaprolactone (PCL), polyethylene glycol (PEG), polymethyl methacrylate (PMMA) sodium alginate (SA), and hydroxyethyl cellulose (HEC).

Benzenesulfonic Acid Salts

In some embodiments, the salt of Compound 1 is the benzenesulfonic acid salt of Compound 1 (Compound 1 Besylate). The benzenesulfonic acid salt of Compound 1 can be crystalline or non-crystalline.

The benzenesulfonic acid salt of Compound 1 Besylate can be prepared by any suitable method for preparation of benzenesulfonic acid addition salts. For example, Compound 1 can be combined with benzenesulfonic acid (e.g., about 1.0 molar eq or more) in a crystallizing solvent and the resulting salt can be isolated by filtering the salt from solution. In certain embodiments, Compound 1 is combined with about 1 to about 2 molar equivalents of benzenesulfonic acid. In certain embodiments, Compound 1 is combined with about 1 to about 1.5 molar equivalents of benzenesulfonic acid. In certain embodiments, Compound 1 is combined with about 1.2 molar equivalents of benzenesulfonic acid.

In some embodiments, Compound 1 Besylate has characteristic XRPD peaks at about 5.8 and about 6.2 degrees 2-theta. In some embodiments, Compound 1 Besylate has at least one characteristic XRPD peak selected from about 5.8 and about 6.2 degrees 2-theta. In some embodiments, Compound 1 Besylate has a characteristic XRPD peak at about 5.8 degrees 2-theta. In some embodiments, Compound 1 Besylate has a characteristic XRPD peak at about 6.2 degrees 2-theta.

In some embodiments, Compound 1 Besylate has at least one characteristic XRPD peak selected from about 5.8, about 6.2, about 12.3, about 16.0, about 18.1, about 18.4, and about 24.7 degrees 2-theta. In some embodiments, Compound 1 Besylate has at least two characteristic XRPD peaks selected from about 5.8, about 6.2, about 12.3, about 16.0, about 18.1, about 18.4, and about 24.7 degrees 2-theta. In some embodiments, Compound 1 Besylate has at least three characteristic XRPD peaks selected from about 5.8, about 6.2, about 12.3, about 16.0, about 18.1, about 18.4, and about 24.7 degrees 2-theta. In some embodiments, Compound 1 Besylate has at least four characteristic XRPD peaks selected from about 5.8, about 6.2, about 12.3, about 16.0, about 18.1, about 18.4, and about 24.7 degrees 2-theta.

Figure 8:
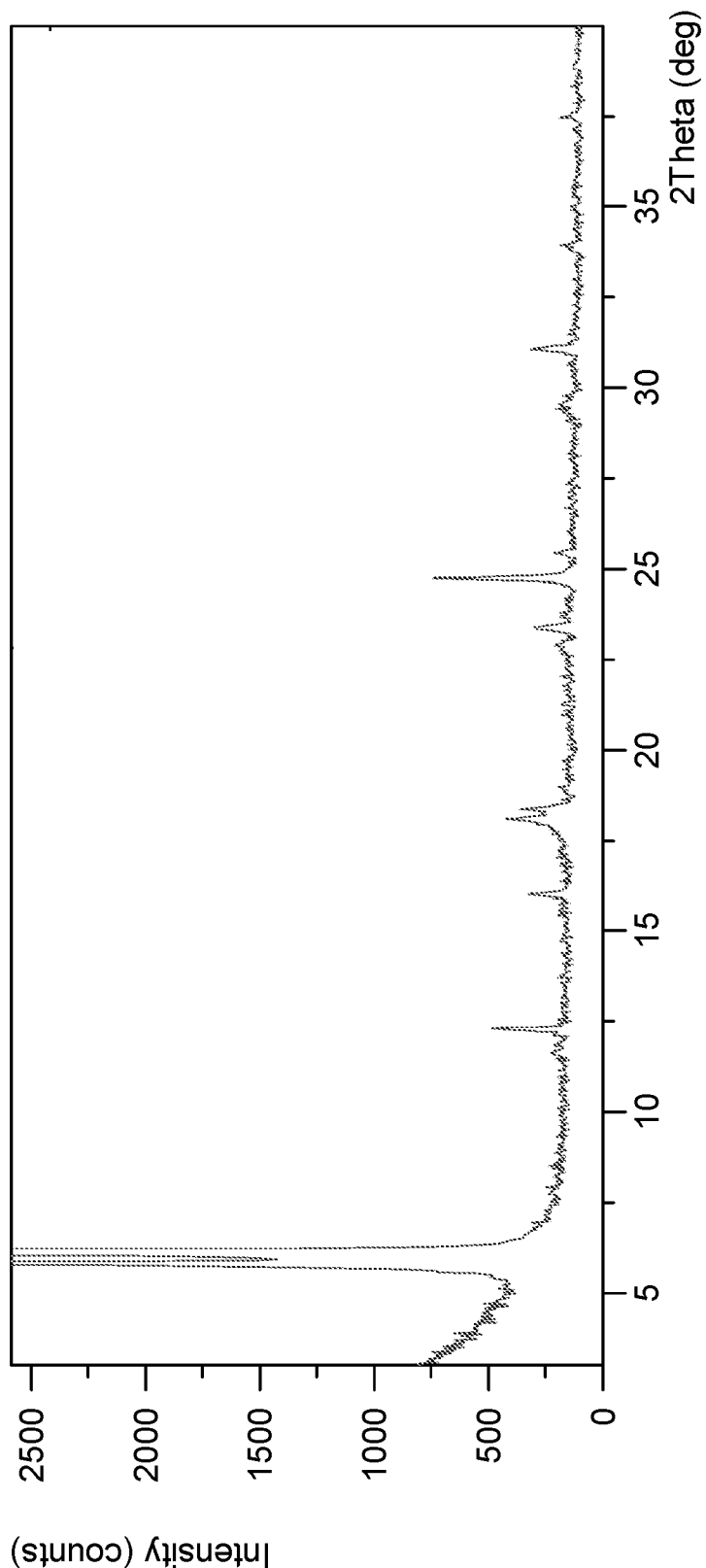
FIG. 8 shows the XRPD pattern of Compound 1 Besylate.

In some embodiments, Compound 1 Besylate has an XRPD pattern with characteristic peaks as substantially shown in FIG. 8.

Figure 9:
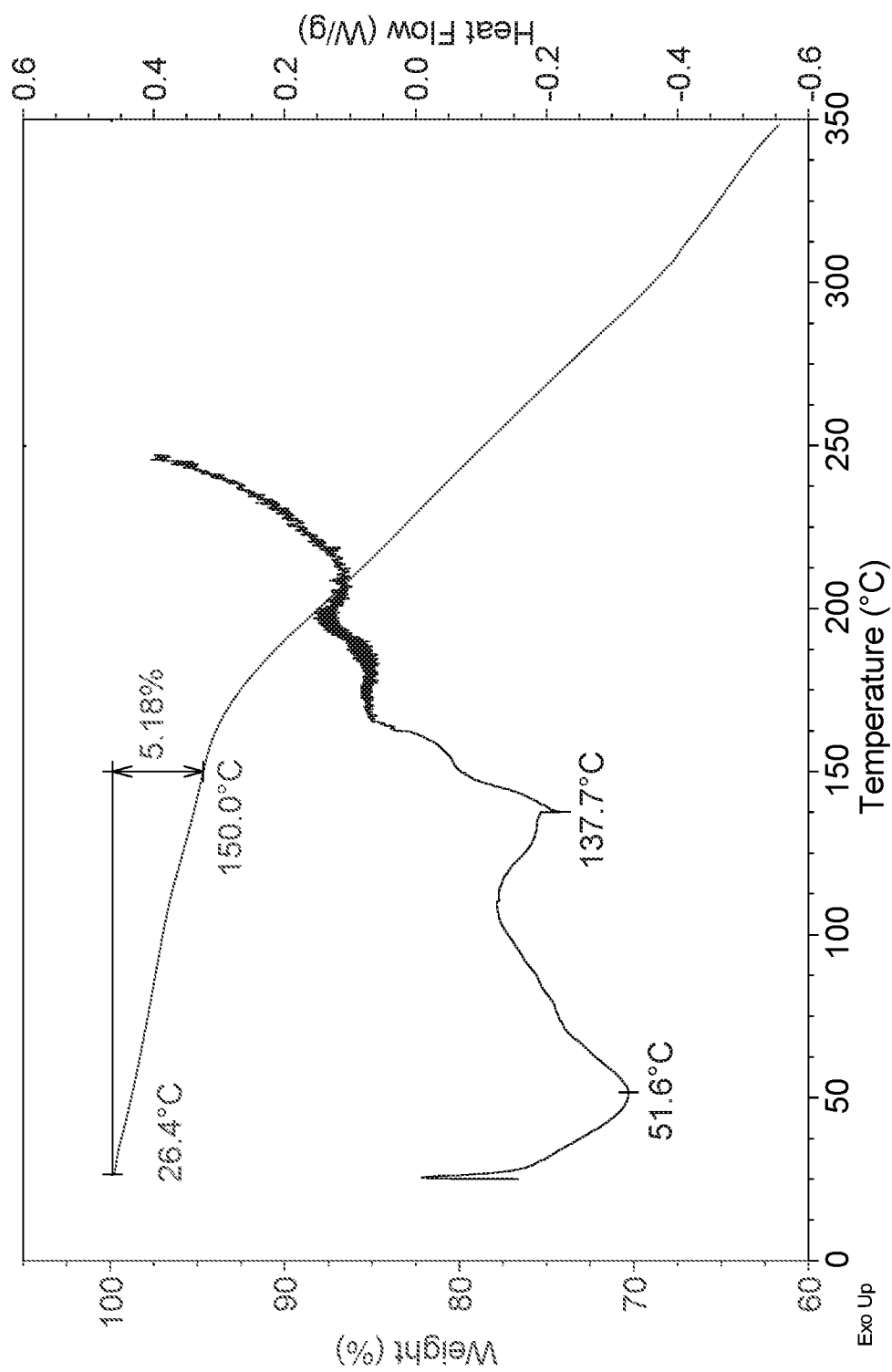
FIG. 9 shows the DSC and TGA thermogram of Compound 1 Besylate.

In some embodiments, Compound 1 Besylate has a DSC thermogram comprising endotherm peaks at temperatures of about 52° C. and about 138° C. In some embodiments, Compound 1 Besylate has a DSC thermogram comprising an endotherm peak at a temperature of about 52° C. In some embodiments, Compound 1 Besylate has a DSC thermogram comprising an endotherm peak at a temperature of about 138° C. In some embodiments, Compound 1 Besylate shows a weight loss of about 5.2% when heated to about 150° C. In some embodiments, Compound 1 Besylate has a DSC thermogram substantially as depicted in FIG. 9. In some embodiments, Compound 1 Besylate has a TGA thermogram substantially as depicted in FIG. 9.

In some embodiments Compound 1 Besylate has at least one characteristic XRPD peak selected from about 5.8 and about 6.2 degrees 2-theta; and has a DSC thermogram comprising an endotherm peak at a temperature of about 52° C. In some embodiments, Compound 1 Besylate has at least one characteristic XRPD peak selected from about 5.8 and about 6.2 degrees 2-theta; and has a DSC thermogram comprising an endotherm peak at a temperature of about 138° C. In some embodiments, Compound 1 Besylate has at least one characteristic XRPD peak selected from about 5.8 and about 6.2 degrees 2-theta; and a DSC thermogram substantially as depicted in FIG. 9.

In some embodiments, Compound 1 Besylate can be isolated with a crystalline purity of at least about 80%, about 85%, about 90%, about 95%, about 96%, about 97%, about 98%, or about 99%. In some embodiments, Compound 1 Besylate can be isolated with a crystalline purity greater than about 99%. In some embodiments, Compound 1 Besylate can be isolated with a crystalline purity greater than about 99.9%. In some embodiments, Compound 1 Besylate is substantially free of other crystalline form. In some embodiments, Compound 1 Besylate is substantially free of amorphous form.

Methods of Use

Compound 1 or salts and solid forms thereof can inhibit the activity of PARP7. For example, Compound 1 or salts and solid forms thereof can be used to inhibit activity of PARP7 in a cell or in an individual or patient in need of inhibition of the enzyme by administering an inhibiting amount of Compound 1 or salts and solid forms thereof to the cell, individual, or patient.

As a PARP7 inhibitor, Compound 1 or salts and solid forms thereof are useful in the treatment of various diseases associated with abnormal expression or activity of PARP7. For example, Compound 1 or salts and solid forms thereof are useful in the treatment of cancer. In some embodiments, the cancers treatable according to the present invention include breast, central nervous system, endometrium, kidney, large intestine, lung, oesophagus, ovary, pancreas, prostate, stomach, head and neck (upper aerodigestive), urinary tract, colon, and others.

In some embodiments, the cancers treatable according to the present invention include hematopoietic malignancies such as leukemia and lymphoma. Example lymphomas include Hodgkin's or non-Hodgkin's lymphoma, multiple myeloma, B-cell lymphoma (e.g., diffuse large B-cell lymphoma (DLBCL)), chronic lymphocytic lymphoma (CLL), T-cell lymphoma, hairy cell lymphoma, and Burkett's lymphoma. Example leukemias include acute lymphocytic leukemia (ALL), acute myelogenous leukemia (AML), chronic lymphocytic leukemia (CLL), and chronic myelogenous leukemia (CML).

Other cancers treatable by the administration of Compound 1 or salts and solid forms thereof include liver cancer (e.g., hepatocellular carcinoma), bladder cancer, bone cancer, glioma, breast cancer, cervical cancer, colon cancer, endometrial cancer, epithelial cancer, esophageal cancer, Ewing's sarcoma, pancreatic cancer, gallbladder cancer, gastric cancer, gastrointestinal tumors, head and neck cancer (upper aerodigestive cancer), intestinal cancers, Kaposi's sarcoma, kidney cancer, laryngeal cancer, liver cancer (e.g., hepatocellular carcinoma), lung cancer, prostate cancer, rectal cancer, skin cancer, stomach cancer, testicular cancer, thyroid cancer, and uterine cancer.

In some embodiments, the cancer treatable by administration of Compound 1 or salts and solid forms thereof is multiple myeloma, DLBCL, hepatocellular carcinoma, bladder cancer, esophageal cancer, head and neck cancer (upper aerodigestive cancer), kidney cancer, prostate cancer, rectal cancer, stomach cancer, thyroid cancer, uterine cancer, and breast cancer.

Compound 1 or salts and solid forms thereof may also have therapeutic utility in PARP7-related disorders in disease areas such as cardiology, virology, neurodegeneration, inflammation, and pain, particularly where the diseases are characterized by overexpression or increased activity of PARP7.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" PARP7 or "contacting" a cell with Compound 1 or salts and solid forms thereof includes the administration of Compound 1 or salts and solid forms thereof to an individual or patient, such as a human, having PARP7, as well as, for example, introducing Compound 1 or salts and solid forms thereof into a sample containing a cellular or purified preparation containing PARP7.

As used herein, the term "individual" or "patient," used interchangeably, refers to mammals, and particularly humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease in an individual who is experiencing or displaying the pathology or symptomatology of the disease (i.e., arresting further development of the pathology and/or symptomatology), or 2) ameliorating the disease in an individual who is experiencing or displaying the pathology or symptomatology of the disease (i.e., reversing the pathology and/or symptomatology).

As used herein the term "preventing" or "prevention" refers to preventing the disease in an individual who may be predisposed to the disease but does not yet experience or display the pathology or symptomatology of the disease.

Combination Therapies

One or more additional pharmaceutical agents or treatment methods such as, for example, chemotherapeutics or other anti-cancer agents, immune enhancers, immunosuppressants, immunotherapies, radiation, anti-tumor and anti-viral vaccines, cytokine therapy (e.g., IL2, GM-CSF, etc.), and/or kinase (tyrosine or serine/threonine), epigenetic or signal transduction inhibitors can be used in combination with Compound 1 or salts and solid forms thereof. The agents can be combined with Compound 1 or salts and solid forms thereof in a single dosage form, or the agents can be administered simultaneously or sequentially as separate dosage forms.

Suitable agents for use in combination with Compound 1 or salts and solid forms thereof for the treatment of cancer include chemotherapeutic agents, targeted cancer therapies, immunotherapies or radiation therapy. Compound 1 or salts and solid forms thereof may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with Compound 1 or salts and solid forms thereof. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Angiogenesis inhibitors may be efficacious in some tumors in combination with Compound 1 or salts and solid forms thereof. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other anti-cancer agent(s) include antibody therapeutics to checkpoint or costimulatory molecules such as CTLA-4, PD-1, PD-L1 or 4-1BB, respectively, or antibodies to cytokines (IL-10, TGF-β, etc.). Exemplary cancer immunotherapy antibodies include pembrolizumab, ipilimumab, nivolumab, atezolizumab and durvalumab. Additional anti-cancer agent(s) include antibody therapeutics directed to surface molecules of hematological cancers such as ofatumumab, rituximab and alemtuzumab.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

Formulation, Dosage Forms and Administration

When employed as pharmaceuticals, Compound 1 or salts and solid forms thereof can be administered in the form of pharmaceutical compositions. A pharmaceutical composition refers to a combination of Compound 1 or salts and solid forms thereof, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be oral, topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, or parenteral.

This invention also includes pharmaceutical compositions which contain, as the active ingredient, one or more of Compound 1 or salts and solid forms thereof in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The compositions can be formulated in a unit dosage form. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of Compound 1 or salts and solid forms thereof. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which Compound 1 or salts and solid forms thereof and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration.

The therapeutic dosage of Compound 1 or salts and solid forms thereof can vary according to, for example, the particular use for which the treatment is made, the manner of administration of Compound 1 or salts and solid forms thereof, the health and condition of the patient, and the judgment of the prescribing physician. The proportion or concentration of a Compound 1 in a pharmaceutical composition can vary depending upon a number of factors including dosage, chemical characteristics (e.g., hydrophobicity), and the route of administration. For example, Compound 1 or salts and solid forms thereof can be provided in an aqueous physiological buffer solution containing about 0.1 to about 10% w/v of Compound 1 or salts and solid forms thereof for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, formulation of the excipient, and its route of administration. Effective doses can be extrapolated from dose-response curves derived from in vitro or animal model test systems.

Compound 1 or salts and solid forms thereof can also be formulated in combination with one or more additional active ingredients which can include any pharmaceutical agent such as anti-viral agents, anti-cancer agents, vaccines, antibodies, immune enhancers, immune suppressants, anti-inflammatory agents and the like.

EXAMPLES

Equipment: $^1$H NMR Spectra were recorded at 300 or 400 MHz using a Bruker AVANCE 300 MHz/400 MHz spectrometer. NMR interpretation was performed using Bruker Topspin software to assign chemical shift and multiplicity. In cases where two adjacent peaks of equal or unequal height were observed, these two peaks may be labeled as either a multiplet or as a doublet. In the case of a doublet, a coupling constant using this software may be assigned. In any given example, one or more protons may not be observed due to obscurity by water and/or solvent peaks. LCMS equipment and conditions are as follows:

1. LC (basic condition): Shimadzu LC-20AD, Binary Pump, Diode Array Detector. Column: Kinetex 2.6 µm EVO C18 100 A, 50*3.0 mm, 2.6 um. Mobile phase: A: Water/5 mM $NH_4HCO_3$, B: Acetonitrile. Flow Rate: 1.2 mL/min at 40° C. Detector: 254 nm, 220 nm. Gradient stop time, 2.9 min.

Timetable:

| T (min) | A (%) | B (%) |
|---|---|---|
| 0.01 | 90 | 10 |
| 2.10 | 5 | 95 |
| 2.70 | 5 | 95 |
| 2.90 | 90 | 10 |

2. LC (acidic condition): Shimadzu LC-20AD, Binary Pump, Diode Array Detector. Column: Ascentis Express C18, 50*3.0 mm, 2.7 um. Mobile phase: A: Water/0.05% TFA, B: Acetonitrile/0.05% TFA. Flow Rate: 1.5 mL/min at 40° C. Detector: 254 nm, 220 nm. Gradient stop time, 2.9 min.

Timetable:

| T (min) | A (%) | B (%) |
|---|---|---|
| 0.01 | 90 | 5 |
| 2.10 | 5 | 95 |
| 2.70 | 5 | 95 |
| 2.90 | 90 | 5 |

1. S:LCMS-2020, Quadrupole LC/MS, Ion Source: ES-API, TIC: 90-900 m/z, Fragmentor: 60, Drying gas flow: 15 L/min, Nebulizing Gas Flow: 1.5 L/min, Drying gas temperature: 250° C., Vcap: 1100V.
2. Sample preparation: samples were dissolved in ACN or methanol at 1-10 mg/mL, then filtered through a 0.22 μm filter membrane. Injection volume: 1-10 μL.

XRPD Analysis: For XRPD analysis, PANalytical Empyrean/X'Pert3 X-ray powder diffractometers were used. The XRPD parameters used are listed below:

| | XRPD Parameters | | |
|---|---|---|---|
| Parameters | CPE-026 (Reflection Mode) | CPE-135 (Reflection Mode) | CPE-221 (Reflection Mode) |
| Model | Empyrean | X' Pert3 | X' Pert3 |
| X-Ray wavelength | Cu, kα, Kα1 (Å): 1.540598, Kα2 (Å): 1.544426 Kα2/Kα1 intensity ratio: 0.50 | Cu, kα, Kα1 (Å): 1.540598, Kα2 (Å): 1.544426 Kα2/Kα1 intensity ratio: 0.50 | Cu, kα, Kα1 (Å): 1.540598, Kα2 (Å): 1.544426 Kα2/Kα1 intensity ratio: 0.50 |
| X-Ray tube setting | 45 kV, 40 mA | 45 kV, 40 mA | 45 kV, 40 mA |
| Divergence slit | Automatic | 1/8° | 1/8° |
| Scan mode | Continuous | Continuous | Continuous |
| Scan range (2θ/°) | 3°~40° | 3°~40° | 3°~40° |
| Step size (2θ/°) | 0.0167 | 0.0263 | 0.0263 |
| Scan step time (s) | 17.780 | 46.665 | 39.525 |
| Test time (s) | 5 min 30 s | 5 min 04 s | 4 min 27 s |

The term "2Th" refers to 2-theta. The term "FWIM" refers to full width at half maximum. The term "rel. int." refers to relative intensity.

DSC/TGA Analysis: TGA data were collected using a TA Q5000/Q5500 TGA from TA Instruments. DSC was performed using a TA Q2000/Q2500 DSC from TA Instruments. Detailed parameters used are listed below:

| Parameters for TGA and DSC | | |
|---|---|---|
| Parameters | TGA | DSC |
| Method | Ramp | Ramp |
| Sample pan | Aluminum, open | Aluminum, crimped |
| Temperature | RT-desired temperature | 25° C.-desired temperature |
| Heating rate | 10° C./min | 10° C./min |
| Purge gas | $N_2$ | $N_2$ |

DVS Analysis: DVS was measured via a SMS (Surface Measurement Systems) DVS Intrinsic. The relative humidity at 25° C. were calibrated against deliquescence point of LiCl, Mg $(NO_3)_2$ and KCl. Parameters for DVS test are listed below:

| Parameters for DVS test | |
|---|---|
| Parameters | DVS |
| Temperature | 25° C. |
| Sample size | 10~20 mg |
| Gas and flow rate | $N_2$, 200 mL/min |
| dm/dt | 0.002%/min |
| Min. dm/dt stability duration | 10 min |
| Max. equilibrium time | 180 min |
| RH range | 95% RH-0% RH-95% RH |
| RH step size | 10% (90% RH-0% RH-90% RH) |
| | 5% (95% RH-90% RH and 90% RH-95% RH) |

RH = relative humidity.
dm/dt = rate of change in moisture content over time.

Definitions: ACN (acetonitrile); $Boc_2O$ (di-tert-butyl dicarbonate); CuI (copper iodide); $CH_3CN$ (acetonitrile); $CDCl_3$ (deuterated chloroform); $CD_3OD$ (deuterated methanol); $CHCl_3$ (chloroform); $Cs_2CO_3$ (cesium carbonate); DCM (dichloromethane); DMF (N,N-dimethylformamide); DMAc (N,N-dimethyl acetamide); DMSO (dimethylsulfoxide); DMSO-$d_6$ (deuterated dimethylsulfoxide); eq (equivalent); EtOAc (ethyl acetate); EtOH (ethanol); g (gram); h (hour); (HATU (1-[bis(dimethylamino)methylene]-1H-1,2,3-triazolo[4,5-b]pyridinium 3-oxide hexafluorophosphate); HOBT (hydroxybenzotriazole); $^1$H NMR (proton nuclear magnetic resonance); HCl (hydrochloric acid); Hz (hertz); IPA (iso-propyl alcohol); IPAc (iso-propyl acetate); $K_2CO_3$ (potassium carbonate); L (litre); LCMS (liquid chromatography-mass spectrometry); M (molar); 2-MeTHF (2-methyl tetrahydrofuran); MeOH (methanol); mg (milligrams); MHz (megahertz); min (minutes); MIBK (methyl iso-butyl ketone); MtBE (methyl tert-butyl ether); MTBE (methyl tert-butyl ether), mL (millilitres), mmol (millimoles); NaCl (sodium chloride); NaH (sodium hydride); NMP (N-methyl-2-pyrrolidone); prep-HPLC (preparative high-performance liquid chromatography); ppm (parts per million); PMB (4-methoxy benzyl); RT (room temperature); TEA (triethyl amine); THF (tetrahydrofuran); TfOH (trifluoromethanesulfonic acid); TFA (trifluoroacetic acid); TLC (thin layer chromatography); TMSI (iodotrimethyl silane); v/v (volume/volume).

Synthesis of Intermediates

Int-A1: 5-Chloro-2-(4-methoxybenzyl)-4-(trifluoromethyl)pyridazin-3(2H)-one

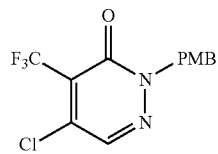

Step 1: 4,5-Dibromo-2-[(4-methoxyphenyl)methyl]-2,3-dihydropyridazin-3-one

To a solution of 4,5-dibromo-2,3-dihydropyridazin-3-one (250 g, 984.71 mmol, 1 equiv) in DMF (2.5 L) was added NaH (59.1 g, 1477.07 mmol, 1.50 equiv, 60%) in several batches at 0-10° C. followed by the addition of 1-(chloromethyl)-4-methoxybenzene (230.3 g, 1470.53 mmol, 1.49 equiv) at 0° C. The resulting solution was stirred for 3 h at RT. The reaction was then quenched by the addition of 5 L of water/ice and extracted with 2×2.5 L of DCM. The organic layers were combined and concentrated. The solids were washed by MeOH (500 mL×2) to afford 290 g (79%) of title compound as a solid. LCMS [M+H]$^+$ 378.00.

Step 2: 5-Methoxy-2-[(4-methoxyphenyl)methyl]-4-(trifluoromethyl)-2,3-dihydropyridazin-3-one A solution of 4,5-dibromo-2-[(4-methoxyphenyl)methyl]-2,3-dihydropyridazin-3-one (290 g, 775.33 mmol, 1 equiv), potassium hydroxide (130.5 g, 2326.00 mmol, 3.00 equiv) in MeOH (2.5 L) was stirred for 2 h at RT. The resulting mixture was concentrated to 500 mL and the solids were collected by filtration. The resulting cake was slurried for 1 h in water (1 L) to afford 232 g (92%) of title compound as a solid. LCMS [M+H]$^+$ 326.90.

Step 3: 5-Methoxy-2-[(4-methoxyphenyl)methyl]-4-(trifluoromethyl)-2,3-dihydropyridazin-3-one A solution of 4-bromo-5-methoxy-2-[(4-methoxyphenyl)methyl]-2,3-dihydropyridazin-3-one (232 g, 713.49 mmol, 1 equiv), methyl 2,2-difluoro-2-sulfoacetate (411.2 g, 2140.44 mmol, 3.00 equiv), and CuI (67.9 g, 356.52 mmol, 0.50 equiv) in NMP (1.2 L) was stirred for 3 h at 100° C. The reaction was then quenched by the addition of 1.5 L of water. The resulting solution was extracted with 3×1 L of DCM. The organic layers were combined and concentrated. The residue was applied onto a silica gel column with EtOAc/petroleum ether (1/1). The collected fractions were combined and concentrated to afford the crude oil to which was added 1 L of water. The solids were collected by filtration and washed with 100 mL of MeOH to afford 170 g (76%) of title compound as a solid. LCMS [M+H]$^+$ 315.10.

Step 4: 5-Hydroxy-2-[(4-methoxyphenyl)methyl]-4-(trifluoromethyl)-2,3-dihydropyridazin-3-one To a solution of 5-methoxy-2-[(4-methoxyphenyl)methyl]-4-(trifluoromethyl)-2,3-dihydropyridazin-3-one (170 g, 540.95 mmol, 1 equiv) in DMF (850 mL) was added TMSI (140 g, 699.67 mmol, 1.29 equiv) dropwise at 20° C. The resulting solution was stirred for 20 h at 85° C. The reaction mixture was then quenched by the addition of 850 mL of water and the resulting solution was extracted with 3×850 mL of DCM and the organic layers combined and dried over anhydrous sodium sulfate. The organic layers were concentrated under vacuum and the crude product was purified by silica gel column chromatography and then recrystallized with MtBE to afford 120 g (74%) of title compound as a white solid. LCMS [M+H]$^+$ 301.07.

Step 5: 5-Chloro-2-[(4-methoxyphenyl)methyl]-4-(trifluoromethyl)-2,3-dihydropyridazin-3-one (Int-A1)

To a solution of 5-hydroxy-2-[(4-methoxyphenyl)methyl]-4-(trifluoromethyl)-2,3-dihydropyridazin-3-one (110 g, 366.38 mmol, 1 equiv) in DMF (550 mL) was added oxalic dichloride (93 g, 732.75 mmol, 2.00 equiv) dropwise at 0-5° C. The resulting solution was stirred for 8 h at RT. The reaction was then quenched by the addition of 550 mL of water. The solids were collected by filtration to afford 108 g (93%) of title compound as a white solid. LCMS [M+H]$^+$ 319.04 [M+H]$^+$, $^1$H NMR (30 MHz, DMSO-d$_6$) δ 8.22 (d, J=0.8 Hz, 1H), 7.33-7.22 (m, 2H), 6.94-6.84 (m, 2H), 5.18 (s, 2H), 3.71 (s, 3H).

Example 1. Synthesis of Compound 1

Step 1: Tert-butyl 4-[5-(trifluoromethyl)pyrimidin-2-yl]piperazine-1-carboxylate A solution of 2-chloro-5-(trifluoromethyl)pyrimidine (100 g, 550 mmol, 1.05 equiv), tert-butyl piperazine-1-carboxylate (96.7 g, 520 mmol, 1 equiv), and K$_2$CO$_3$ (151.8 g, 1100 mmol, 2 equiv) in NMP (800 mL) was stirred for 1 h at 80° C. followed by the addition of 2.5 L of H$_2$O. The solids were collected by filtration to afford 190 g (94%) of the title compound as a white solid. LCMS: [M+H]$^+$ 333.16.

Step 2: 2-(Piperazin-1-yl)-5-(trifluoromethyl)pyrimidine dihydrochloride

A solution of tert-butyl 4-[5-(trifluoromethyl)pyrimidin-2-yl]piperazine-1-carboxylate (190 g, 571.73 mmol, 1 equiv) in HCl/dioxane (800 mL/4M) was stirred for 1 h at RT. The solids were collected by filtration to afford 154 g (99%) of the title compound as a white solid. LCMS: [M+H]$^+$ 199.08.

Step 3: 1-(4-(5-Trifluoromethyl)pyrimidin-2-yl)piperazin-1-yl)prop-2-en-1-one A solution of 2-(piperazin-1-yl)-5-(trifluoromethyl)pyrimidine dihydrochloride (300 g, 1.1 mol, 1 equiv), prop-2-enoyl prop-2-enoate (156 g, 1.24 mol, 1.1 equiv) and TEA (375 g, 3.71 mol, 3.3 equiv) in DCM (2.5 L) was stirred for 30 min at −40° C. 2 L of DCM was added to the resulting solution after the reaction completed and the resulting solution was extracted with 2×1 L of water. The organic layer was concentrated and the residue was applied onto a silica gel column eluting with EtOAc/petroleum ether (1/4). The collected fractions were combined and concentrated to afford 200 g (62.6%) of title compound as a white solid. LCMS: [M+H]$^+$ 287.23.

Step 4: (S)-Tert-butyl 1-(3-oxo-3-(4-(5-(trifluoromethyl)pyrimidin-2-yl)piperazin-1-yl)propoxy)propan-2-ylcarbamate A solution of tert-butyl N-[(2S)-1-hydroxypropan-2-yl]carbamate (244 g, 1.39 mol, 2 equiv), 1-(4-(5-(trifluoromethyl)pyrimidin-2-yl)piperazin-1-yl)prop-2-en-1-one (200 g, 699 mmol, 1 equiv), and Cs$_2$CO$_3$ (273 g, 838 mmol, 1.2 equiv) in CH$_3$CN (1.4 L) was stirred for 24 h at 25° C. The solids were filtered and the filtrate was concentrated under reduced pressure. The residue was applied onto a silica gel column eluting with EtOAc/petroleum ether (1/3) to afford 257 g (80%) of title compound as a white solid. LCMS: [M+H]$^+$ 462.27.

Step 5: (S)-3-(2-Aminopropoxy)-1-(4-(5-(trifluoromethyl)pyrimidin-2-yl)piperazin-1-yl)propan-1-one A solution of 1-(4-(5-(trifluoromethyl)pyrimidin-2-yl)piperazin-1-yl)prop-2-en-1-one (257 g, 557 mmol, 1 equiv) and dioxane/HCl (4 mol/L, 1 L) was stirred for 2 h at 25° C. The pH value of the reaction mixture was adjusted to 7 by the addition of NaOH (aqueous). After concentration under reduced pressure, the residue was purified by C18 reverse phase chromatography eluting with H$_2$O/CH$_3$CN to afford 167 g (83.0%) of title compound as a white solid. LCMS: [M+H]$^+$ 362.34.

Step 6: (S)-2-(4-Methoxybenzyl)-5-(1-(3-oxo-3-(4-(5-(trifluoromethyl)pyrimidin-2-yl)piperazin-1-yl)propoxy)propan-2-ylamino)-4-(trifluoromethyl)pyridazin-3(2H)-one A solution of (S)-3-(2-aminopropoxy)-1-(4-(5-(trifluoromethyl)pyrimidin-2-yl)piperazin-1-yl)propan-1-one (167 g, 462 mmol, 1 equiv), Int-A1 (161 g, 505 mmol, 1.1 equiv), and TEA (210 g, 2.08 mol, 4.5 equiv) in CH$_3$CN (1.2 L) was stirred for 6 h at 25° C. The solids were filtered and the filtrate was combined and concentrated under reduced pressure. The residue was applied onto a silica gel column with EtOAc/petroleum ether (1/1) to afford 230 g (77.3%) of title compound as a white solid. LCMS: [M+H]$^+$ 644.41.

Step 7: 5-[[(2S)-1-(3-oxo-3-[4-[5-(trifluoromethyl) pyrimidin-2-yl]piperazin-1-yl]propoxy)propan-2-yl] amino]-4-(trifluoromethyl)-2,3-dihydropyridazin-3-one A solution of (S)-2-(4-methoxybenzyl)-5-(1-(3-oxo-3-(4-(5-(trifluoromethyl)pyrimidin-2-yl)piperazin-1-yl)propoxy) propan-2-ylamino)-4-(trifluoromethyl)pyridazin-3(2H)-one (230 g, 358 mmol, 1 equiv) and TfOH (115 mL) in TFA (1.0 L) was stirred for 2 h at 25° C. The reaction was then quenched by the addition of 4.0 L of water. The resulting solution was extracted with 2×1 L of EtOAc. The pH value of the organic layers was adjusted to 8 by aqueous K$_2$CO$_3$ solution. The organic layer was combined and concentrated. The residue was applied onto a silica gel column with EtOAc/petroleum ether (4/1). The fractions were combined and concentrated followed by further washing with EtOAc to afford 114 g (61.2%) of title compound as a white crystalline solid. LCMS: [M+H]$^+$ 524.25[M+H]$^+$, $^1$H NMR (400 MHz, DMSO-d$_6$) δ: 12.45 (s, 1H), 8.73 (s, 2H), 7.91 (s, 1H), 6.29-6.26 (m, 1H), 4.12-4.19 (m, 1H), 3.81-3.85 (m, 4H), 3.73-3.79 (m, 2H), 3.54-3.69 (m, 6H), 2.60 (t, J=9.2 Hz, 2H), 1.16 (d, J=12.4 Hz, 3H).

The resulting white crystalline solid corresponds to Compound 1 Form A, which is further characterized in Example 2.

Example 2. Characterization of Form A

The solid product from Example 1, Step 7 (Compound 1) was confirmed as a crystalline solid according to XRPD analysis, and referred to herein as Form A. The XRPD pattern of Form A is shown in FIG. 1 and the peak data is given below in Table 1.

TABLE 1

XRPD Peak Data for Form A.

| Pos. [° 2Th.] | Height [cts] | FWHM Left [° 2Th.] | d-spacing [Å] | Rel. Int. [%] |
|---|---|---|---|---|
| 5.8 | 929.0 | 0.1 | 15.4 | 33.0 |
| 10.8 | 932.8 | 0.1 | 8.2 | 33.1 |
| 11.2 | 202.2 | 0.1 | 7.9 | 7.2 |
| 11.9 | 791.4 | 0.2 | 7.5 | 28.1 |
| 12.3 | 213.6 | 0.1 | 7.2 | 7.6 |
| 13.3 | 515.1 | 0.1 | 6.7 | 18.3 |
| 13.5 | 437.1 | 0.1 | 6.6 | 15.5 |
| 13.8 | 172.1 | 0.1 | 6.4 | 6.1 |
| 15.5 | 541.5 | 0.1 | 5.7 | 19.2 |
| 15.8 | 270.0 | 0.1 | 5.6 | 9.6 |
| 16.6 | 127.7 | 0.1 | 5.4 | 4.5 |
| 17.2 | 2814.9 | 0.1 | 5.1 | 100.0 |
| 17.7 | 645.6 | 0.1 | 5.0 | 22.9 |
| 18.0 | 611.5 | 0.1 | 4.9 | 21.7 |
| 18.4 | 417.5 | 0.1 | 4.8 | 14.8 |
| 18.7 | 163.9 | 0.1 | 4.7 | 5.8 |
| 19.5 | 604.9 | 0.1 | 4.5 | 21.5 |
| 20.1 | 278.7 | 0.1 | 4.4 | 9.9 |
| 20.5 | 506.0 | 0.1 | 4.3 | 18.0 |
| 21.0 | 1121.6 | 0.1 | 4.2 | 39.9 |
| 21.6 | 2094.1 | 0.1 | 4.1 | 74.4 |
| 21.8 | 1357.3 | 0.1 | 4.1 | 48.2 |
| 22.1 | 851.6 | 0.1 | 4.0 | 30.3 |
| 22.4 | 613.7 | 0.1 | 4.0 | 21.8 |
| 22.7 | 1295.5 | 0.1 | 3.9 | 46.0 |
| 23.0 | 2760.9 | 0.1 | 3.9 | 98.1 |
| 23.4 | 1332.8 | 0.1 | 3.8 | 47.4 |
| 24.2 | 379.7 | 0.1 | 3.7 | 13.5 |
| 24.7 | 349.2 | 0.2 | 3.6 | 12.4 |
| 24.9 | 1343.4 | 0.1 | 3.6 | 47.7 |
| 25.5 | 125.9 | 0.1 | 3.5 | 4.5 |
| 26.2 | 113.9 | 0.1 | 3.4 | 4.1 |
| 26.7 | 449.2 | 0.1 | 3.3 | 16.0 |
| 27.5 | 93.8 | 0.2 | 3.2 | 3.3 |
| 28.0 | 176.1 | 0.1 | 3.2 | 6.3 |
| 28.7 | 136.0 | 0.2 | 3.1 | 4.8 |
| 30.8 | 272.1 | 0.1 | 2.9 | 9.7 |
| 31.4 | 138.3 | 0.3 | 2.8 | 4.9 |
| 32.7 | 79.4 | 0.2 | 2.7 | 2.8 |
| 36.5 | 40.6 | 0.3 | 2.5 | 1.4 |

Form A exhibits a DSC thermogram having an endotherm peak at a temperature of about 174° C. Form A shows a weight loss of about 0.5% when heated to 150° C. FIG. 2 shows a DSC thermogram and a TGA thermogram of Compound 1 Form A. FIG. 3 shows a DVS isotherm of Compound 1 Form A. The data suggest that Form A may be an anhydrous crystalline form.

Example 3. Solubility of Form A

The approximate solubility of Form A was estimated in 27 solvents or co-solvents at room temperature. Approximately 2 mg of solids were weighed into each 3 mL glass vial, to which each of the solvents was added in stepwise until the solids dissolved completely or the total volume reaches 2.0 mL. Solubility ranges were used to guide the solvent selection for polymorph screening described in later examples.

TABLE 2

Approximate solubility of Form A

| Solvent | Solubility (mg/mL) | Solvent (v:v) | Solubility (mg/mL) |
|---|---|---|---|
| MeOH | S < 1.1 | n-Heptane | S < 1.0 |
| EtOH | S < 1.1 | Toluene | S < 1.0 |
| IPA | S < 1.1 | DMAc | 22.0 < S < 44.0 |
| Acetone | S > 40.0 | DMSO | S > 42.0 |
| MIBK | S < 1.0 | NMP | S > 38.0 |
| EtOAc | 1.9 < S < 4.8 | H$_2$O | S < 1.1 |
| IPAc | S < 1.1 | Acetone/n-Heptane (1:4) | S < 1.3 |
| MTBE | S < 1.0 | Acetone/n-Heptane (1:9) | S < 1.0 |
| THF | S < 1.1 | DCM/MTBE (1:9) | S < 1.2 |
| 2-MeTHF | S < 1.0 | ACN/MTBE (1:9) | 1.2 < S < 2.4 |
| 1,4-Dioxane | 5.0 < S < 10.0 | ACN/MIBK (1:9) | 2.0 < S < 5.0 |
| ACN | 11.0 < S < 22.0 | ACN/THF (1:4) | 5.0 < S < 10.0 |
| CHCl$_3$ | 22.0 < S < 44.0 | ACN/THF (1:9) | 10.0 < S < 20.0 |
| DCM | 19.0 < S < 38.0 | — | — |

S = solubility

Example 4. Polymorph Screening—Anti-Solvent Addition

A total of 12 anti-solvent addition experiments were carried out. About 15 mg of Form A was dissolved in 0.5-2.5 mL solvent to obtain a clear solution and the solution was magnetically stirred (ca. 1000 rpm) followed by addition of 0.1 mL anti-solvent per step until precipitate appeared or the total amount of anti-solvent reached 10 mL. The obtained precipitate was isolated for XRPD analysis. Results in Table 3 showed that Form A, Form B, and Form C were obtained.

TABLE 3

Summary of anti-solvent addition experiments

| Solvent | Anti-solvent | Solid Form |
|---|---|---|
| Acetone | 2-MeTHF | Form C* |
|  | IPAc | Form A* |
|  | n-heptane | Form A |
| DCM | MTBE | Form A* |
|  | EtOH | Form A* |
|  | THF | Form C* |
| DMAc | H$_2$O | Form A |
|  | toluene | Form A* |
| CHCl$_3$ | n-heptane | Form B |
| ACN | IPA | Form A* |
|  | MIBK | Form A* |
| NMP | H$_2$O | Form A |

*Clear solutions were obtained after anti-solvent addition and stirring at 5° C., which were transferred to evaporate at RT.

Example 5. Polymorph Screening—Reverse Anti-Solvent Addition

Reverse anti-solvent addition experiments were conducted under 10 conditions. Approximately 15 mg of Form A were dissolved in 0.5-1.5 mL of each solvent to obtain a clear solution. This solution was added drop-wise into a glass vial containing 4 mL of each anti-solvent at RT. The precipitate was isolated for XRPD analysis. The results summarized in Table 4 showed that Form A, B and C were obtained.

TABLE 4

Summary of reverse anti-solvent addition experiments

| Solvent | Anti-solvent | Solid Form |
|---|---|---|
| ACN | MTBE | Form A* |
|  | toluene | Form A* |
|  | THF | Form C* |
| CHCl$_3$ | MeOH | Form A + C* |
|  | MIBK | Form A* |
|  | IPAc | Form B + C* |
| DMSO | n-heptane | Form A* |
|  | H$_2$O | Form A |
| Acetone | toluene | Form A* |
| DCM | IPA | Form A* |

*Clear solutions were obtained after reverse anti-solvent addition and stirring at 5° C., which were transferred to evaporate at RT.

Example 6. Polymorph Screening—Slow Evaporation

Slow evaporation experiments were performed under 10 conditions. Briefly, about 15 mg of Form A were dissolved in 0.5-2.0 mL of each solvent in a 3-mL glass vial. The suspensions were filtered using a PTFE membrane (pore size of 0.45 μm) and the filtrates were used for the follow-up steps. The visually clear solutions were subjected to evaporation at RT and vials sealed with Parafilm® (poked with 5 pin-holes). The solids were isolated for XRPD analysis, and the results summarized in Table 5 indicated that Form A, B and C were obtained.

TABLE 5

Summary of slow evaporation experiments

| Solvent (v:v) | Solid Form |
|---|---|
| Acetone | Form A |
| CHCl$_3$ | Form B |
| DCM | Form A |
| ACN | Form A |
| 1,4-dioxane | Form A |
| Acetone/H$_2$O (4:1) | Form C |
| DCM/MTBE (1:1) | Form C |
| ACN/THF (1:1) | Form C |
| CHCl$_3$/EtOAc (1:1) | Form A |
| 1,4-dioxane/MeOH (4:1) | Form A |

Example 7. Polymorph Screening—Slow Cooling

Slow cooling experiments were conducted in 7 solvent systems. About 15 mg of Form A were suspended in 0.5 mL of solvent in an HPLC vial at RT. The suspension was then heated to 50° C., equilibrated for about 2 hours and filtered into a new vial using a PTFE membrane (pore size of 0.45 m) if not completely dissolved. Filtrates were slowly cooled down to 5° C. at a rate of 0.1° C./min. The obtained solids were kept isothermal at 5° C. before isolated for XRPD analysis. Clear solutions were evaporated to dryness at RT and then solids were tested by XRPD. Results summarized in Table 6 indicated Form A, Form C and amorphous solid were obtained.

TABLE 6

Summary of slow cooling experiments

| Solvent (v:v) | Solid Form |
|---|---|
| EtOAc | Form A |
| acetone/IPA (1:4) | Form A* |
| ACN/THF (1:4) | Form C* |
| DCM/MIBK (1:9) | Form A* |
| CHCl$_3$/IPAc (1:9) | Form A |
| ACN/MIBK (1:9) | Form A* |
| DMAc/H$_2$O (1:4) | Amorphous* |

*Clear solutions were obtained after cooling at 5° C. or −20° C., which were transferred to evaporate at RT.

Example 8. Slurry Cycling (50-5° C.)

Slurry cycling (50-5° C.) experiments were conducted in 11 different solvent systems. About 15 mg of Form A were suspended in 0.5 mL of solvent in an HPLC vial. The suspensions were magnetically stirred (ca. 1000 rpm) at 50° C. for 2 hours and then slowly cooled down to 5° C. at a rate of 0.1° C./min. The obtained solids were kept isothermal at 5° C. after being cycled between 50° C. and 5° C. twice. Solids were isolated for XRPD analysis. Results summarized in Table 7 indicate that only Form A was generated.

TABLE 7

Summary of slurry cycling (50-5° C.) experiments

| Solvent (v:v) | Solid Form |
|---|---|
| EtOH | Form A |
| MIBK | Form A |
| IPAc | Form A |
| MTBE | Form A |
| 2-MeTHF | Form A |

TABLE 7-continued

Summary of slurry cycling (50-5° C.) experiments

| Solvent (v:v) | Solid Form |
|---|---|
| 1,4-dioxane | Form A |
| toluene | Form A |
| H$_2$O | Form A |
| ACN/n-heptane (1:9) | Form A |
| IPA/EtOAc (4:1) | Form A |
| NMP/toluene (1:9) | Form A |

Example 9. Polymorph Screening—Slurry at Room Temperature

Slurry conversion experiments were conducted at RT in 13 different solvent systems. Briefly, about 15 mg of Form A were suspended in 0.5 mL of solvent in an HPLC vial. After the suspension was stirred magnetically (ca. 1000 rpm) for about 3 days at RT, the remaining solids were isolated for XRPD analysis. Results summarized in Table 8 indicated that only Form A or amorphous was generated.

TABLE 8

Summary of slurry conversion experiments at RT

| Solvent (v:v) | Solid Form |
|---|---|
| MeOH | Amorphous* |
| IPA | Form A |
| MTBE | Form A |
| EtOAc | Form A |
| THF | Form A** |
| H$_2$O | Form A |
| n-heptane | Form A |
| EtOH/H$_2$O (a$_w$~0.3) | Form A* |
| EtOH/H$_2$O (a$_w$~0.6) | Form A* |
| EtOH/H$_2$O (a$_w$~0.9) | Form A |
| DCM/MTBE (1:9) | Form A |
| ACN/MIBK (1:9) | Form A |
| 1,4-dioxane/2-MeTHF (1:1) | Form A** |

*Clear solutions were obtained after stirring at RT, which were transferred to slurry at 5° C.
**The samples were transferred to RT for evaporation after stirring at 5° C. or −20° C.

Example 10. Polymorph Screening—Slurry at 50° C.

Slurry conversion experiments were also conducted at 50° C. in 11 different solvent systems. About 15 mg of Form A were suspended in 0.5 mL of solvent in an HPLC vial. After the suspension was magnetically stirred (ca. 1000 rpm) for about 3 days at 50° C., the remaining solids were isolated for XRPD analysis. Results summarized in Table 9 indicate that only Form A was generated.

TABLE 9

Summary of slurry conversion experiments at 50° C.

| Solvent (v:v) | Solid Form |
|---|---|
| EtOH | Form A* |
| MIBK | Form A |
| IPAc | Form A |
| MTBE | Form A |
| 2-MeTHF | Form A* |
| H$_2$O | Form A |
| Toluene | Form A |
| NMP/THF (1:9) | Form A** |
| acetone/n-heptane (1:9) | Form A |
| DMAc/H$_2$O (1:9) | Form A |
| ACN/EtOAc (1:9) | Form A* |

*Clear solutions were obtained after stirring at 50° C., which were transferred to slurry at 5° C.
**The sample was transferred to RT for evaporation after stirring at 5° C. or −20° C.

Example 11. Polymorph Screening—Vapor-Solid Diffusion

Nine vapor-solid diffusion experiments were performed using different solvents. About 15 mg of Form A was weighed into a 3-mL glass vial. This 3-mL vial was then placed into a 20-mL vial with 4 mL of solvents. The 20-mL vial was sealed with a cap and kept at RT for 9 days. The solids were isolated for XRPD analysis. The results summarized in Table 10 showed that only Form A was obtained.

TABLE 10

Summary of vapor-solid diffusion experiments

| Solvent | Solid Form |
|---|---|
| MeOH | Form A |
| Acetone | Form A |
| EtOAc | Form A |
| ACN | Form A |
| CHCl$_3$ | Form A* |
| DCM | Form A* |
| H$_2$O | Form A |
| THF | Form A |
| toluene | Form A |

*Clear solutions were obtained and these samples were transferred to RT for evaporation.

Example 12. Polymorph Screening—Vapor-Solution Diffusion

Nine vapor-solution diffusion experiments were conducted. Approximately 15 mg of Form A were dissolved in 0.5-2.5 mL of appropriate solvent to obtain a clear solution in a 3-mL vial. This solution was then placed into a 20-mL vial with 4 mL of volatile solvents. The 20-mL vial was sealed with a cap and kept at RT about 3 days to 8 days for organic vapor to interact with the solution. The solids were isolated for XRPD analysis. The results summarized in Table 11 showed that only Form A or amorphous was observed.

TABLE 11

Summary of vapor-solution diffusion experiments

| Solvent (v:v) | Anti-solvent | Solid Form |
|---|---|---|
| Acetone | MTBE | Form A* |
|  | H$_2$O | Form A |
| ACN | IPAc | Form A* |
|  | THF | Form A* |
| DCM | MIBK | Form A |
| CHCl$_3$ | EtOH | Form A* |

TABLE 11-continued

Summary of vapor-solution diffusion experiments

| Solvent (v:v) | Anti-solvent | Solid Form |
|---|---|---|
| DMAc | toluene | Amorphous** |
| NMP | H$_2$O | NA** |
| ACN/THF (1:1) | MeOH | Form A* |

*Clear solutions were obtained and these samples were transferred to RT for evaporation.
**These samples were further transferred for vacuum drying at RT for 6 days, followed by vacuum drying at 50° C. for 1 day.
NA: No solid was obtained.

Example 13. Polymer Induced Crystallization

Polymer induced crystallization experiments were performed with two sets of polymer mixtures in 8 different solvent systems. Approximately 15 mg of Form A were dissolved in 0.5-2.0 mL of solvent in a 3-mL glass vial. About 2 mg of polymer mixture was added into the 3-mL glass vial. The resulting solutions were subjected to evaporation at RT in vials sealed with Parafilm© (poked with 5 pin-holes) for slow evaporation. The solids were isolated for XRPD analysis. Results summarized in Table 12 showed that Form A, C and amorphous were obtained.

TABLE 12

Summary of polymer induced crystallization experiments

| Solvent (v:v) | Polymer | Solid Form |
|---|---|---|
| Acetone | Polymer A | Form A |
| ACN | | Amorphous |
| CHCl$_3$ | | Form A |
| DCM/MTBE (1:1) | | Form A |
| 1,4-dioxane | Polymer B | Form A |
| DCM | | Form A |
| Acetone/H$_2$O (4:1) | | Form C |
| ACN/THF (1:2) | | Form C + Peak (2θ~15.5°) |

Polymer mixture A: polyvinyl pyrrolidone (PVP), polyvinyl alcohol (PVA), polyvinyl-chloride (PVC), polyvinyl acetate (PVAC), hypromellose (HPMC), methyl cellulose (MC) (mass ratio of 1:1:1:1:1:1).
Polymer mixture B: polycaprolactone (PCL), polyethylene glycol (PEG), polymethyl methacrylate (PMMA), sodium alginate (SA), and hydroxyethyl cellulose (HEC) (mass ratio of 1:1:1:1:1).

Example 14. Characterization of Form B

The XRPD pattern of Form B is shown in FIG. 4 and the peak data is given below in Table 13.

TABLE 13

XRPD Peaks for Form B

| Pos. [°2Th.] | Height [cts] | FWHM Left [°2Th.] | d-spacing [Å] | Rel. Int. [%] |
|---|---|---|---|---|
| 5.7 | 4803.6 | 0.1 | 15.6 | 20.3 |
| 11.3 | 4097.7 | 0.1 | 7.8 | 17.3 |
| 14.1 | 23637.2 | 0.1 | 6.3 | 100.0 |
| 15.7 | 420.1 | 0.2 | 5.6 | 1.8 |
| 16.9 | 12209.8 | 0.1 | 5.2 | 51.7 |
| 19.4 | 234.3 | 0.1 | 4.6 | 1.0 |
| 19.8 | 3730.1 | 0.1 | 4.5 | 15.8 |
| 21.0 | 171.2 | 0.1 | 4.2 | 0.7 |
| 21.5 | 223.5 | 0.1 | 4.1 | 1.0 |
| 22.0 | 350.2 | 0.2 | 4.0 | 1.5 |
| 22.6 | 182.5 | 0.1 | 3.9 | 0.8 |
| 23.7 | 57.2 | 0.3 | 3.7 | 0.2 |
| 25.5 | 3942.3 | 0.1 | 3.5 | 16.7 |
| 26.3 | 206.5 | 0.1 | 3.4 | 0.9 |
| 27.2 | 348.9 | 0.1 | 3.3 | 1.5 |
| 28.4 | 2225.1 | 0.1 | 3.1 | 9.4 |
| 28.8 | 523.4 | 0.1 | 3.1 | 2.2 |
| 30.1 | 43.4 | 0.3 | 3.0 | 0.2 |
| 31.4 | 134.4 | 0.3 | 2.8 | 0.6 |
| 34.2 | 291.3 | 0.2 | 2.6 | 1.2 |
| 35.5 | 109.0 | 0.2 | 2.5 | 0.5 |
| 36.7 | 55.6 | 0.3 | 2.4 | 0.2 |
| 38.3 | 50.3 | 0.2 | 2.3 | 0.2 |

Form B exhibits a DSC thermogram having endotherm peaks at temperatures of about 71° C., about 83° C., about 100° C., and about 172° C. Form B shows a weight loss of about 5.4% when heated to 150° C. FIG. 5 shows a DSC thermogram and a TGA thermogram of Form B.

Example 15. Characterization of Form C

The XRPD pattern of Form C is shown in FIG. 6 and the peak data is given below in Table 14.

TABLE 14

XRPD Peaks for Form C

| Pos. [°2Th.] | Height [cts] | FWHM Left [°2Th.] | d-spacing [Å] | Rel. Int. [%] |
|---|---|---|---|---|
| 8.6 | 101.7 | 0.3 | 10.3 | 0.6 |
| 10.9 | 223.8 | 0.1 | 8.1 | 1.4 |
| 11.8 | 85.2 | 0.3 | 7.5 | 0.5 |
| 15.2 | 81.5 | 0.2 | 5.8 | 0.5 |
| 16.6 | 5037.3 | 0.1 | 5.4 | 30.7 |
| 17.2 | 361.9 | 0.1 | 5.2 | 2.2 |
| 18.8 | 16425.8 | 0.1 | 4.7 | 100.0 |
| 19.2 | 232.8 | 0.1 | 4.6 | 1.4 |
| 21.1 | 267.8 | 0.2 | 4.2 | 1.6 |
| 21.6 | 4968.7 | 0.1 | 4.1 | 30.3 |
| 22.3 | 851.1 | 0.1 | 4.0 | 5.2 |
| 24.6 | 380.4 | 0.1 | 3.6 | 2.3 |
| 24.9 | 1369.3 | 0.1 | 3.6 | 8.3 |
| 26.3 | 173.9 | 0.1 | 3.4 | 1.1 |
| 27.9 | 98.6 | 0.2 | 3.2 | 0.6 |
| 28.5 | 76.5 | 0.2 | 3.1 | 0.5 |
| 30.7 | 194.6 | 0.1 | 2.9 | 1.2 |
| 32.8 | 49.8 | 0.2 | 2.7 | 0.3 |
| 34.6 | 45.4 | 0.3 | 2.6 | 0.3 |
| 35.5 | 366.0 | 0.1 | 2.5 | 2.2 |
| 39.2 | 31.5 | 0.3 | 2.3 | 0.2 |

Form C exhibits a DSC thermogram having an endotherm peak at a temperature of about 159° C. and about 174° C. Form C shows a weight loss of about 1.1% when heated to 150° C. FIG. 7 shows a DSC thermogram and a TGA thermogram of Form C.

Example 16. Salt/Cocrystal Screening

According to the approximate solubility of starting material (Form A), salt/cocrystal screening for Compound 1 was performed under 48 conditions using 8 acids or bases in 6 solvent systems. The starting material (Form A) and corresponding acid or base were added in an HPLC glass vial followed by addition of 0.5 mL solvent. After slurrying (1000 rpm) at RT for 4-5 days, the resulting suspension was centrifuged (10000 rpm, 2 minutes) to retrieve the solids for further XRPD analysis. However, freebase Form A was observed in most of the experiments, so the samples were further slurried at RT or lower temperature for another 2~3 days, and the resulting solids were re-analyzed by XRPD. As summarized in Table 15, only one potential salt/cocrystal hit was obtained, which was named Compound 1 Besylate.

TABLE 15

Summary of salt/cocrystal screening experiments

| | | | | Solvent | | | |
|---|---|---|---|---|---|---|---|
| | Acid/Base | A EtOAc | B 1,4-Dioxane | C EtOH | D ACN/MTBE (1:9) | E Acetone/n-heptane (1:4) | F THF/H$_2$O (9:1) |
| 1 | HCl (1:1) | Amorphous*[1] | Form A* | Form A | Form A* | Form A | Form A** |
| 2 | H$_2$SO$_4$ | Form A* | Form A* | Form A | Form A* | Form A* | Form A** |
| 3 | Methanesulfonic acid | Form A | Amorphous* | Form A | Form A | Form A | Form A + Peak** |
| 4 | Benzenesulfonic acid | Besylate Compound 1 | Besylate Compound 1 | Form A | Form A + Peak | Form A | Form A** |
| 5 | H$_3$PO$_4$ | Form A* | Form A* | Form A | Form A | Form A | Form A** |
| 6 | KOH | Amorphous | Amorphous | Form A | Form A | Form A | Amorphous |
| 7 | NaOH | Form A | Form A | Form A | Form A + Peak | Form A* | Form A** |
| 8 | Ca(OH)$_2$ | Form A + Base | Base | Form A + Base | Form A + Base | Form A + Base | Base |
| 9 | Blank | Form A | Amorphous* | Form A | Form A | Form A | Form A** |

*Clear solutions were obtained, which were transferred to 5° C. for stirring.
**Clear solutions were obtained after stirring at RT or lower temperature, which were transferred to evaporate at RT.
[1]Entries reciting "Amorphous" refer to either amorphous free base, the amorphous salt, or a mixture thereof.

Example 17. Characterization of Compound 1 Besylate

Compound 1 Besylate was prepared according to the following procedure. 31.0 mg of Form A and 9.2 mg of benzenesulfonic acid were added into a 1.5-mL glass vial. 0.5 mL of EtOAc was added into the vial. The sample was stirred at a rate of 1000 r/min on a magnetic stirrer at RT for 5 days, followed by stirring at 5° C. for 2 days. The solids were isolated by centrifugation, to provide Compound 1 Besylate.

The XRPD pattern of Compound 1 Besylate is shown in FIG. 8 and the peak data is given below in Table 16.

TABLE 16

XRPD of Compound 1 Besylate

| Pos. [°2Th.] | Height [cts] | FWHM Left [°2Th.] | d-spacing [Å] | Rel. Int. [%] |
|---|---|---|---|---|
| 5.8 | 3242.4 | 0.1 | 15.2 | 35.9 |
| 6.2 | 9042.3 | 0.1 | 14.4 | 100.0 |
| 12.3 | 292.7 | 0.1 | 7.2 | 3.2 |
| 16.0 | 177.7 | 0.1 | 5.5 | 2.0 |
| 18.1 | 265.4 | 0.1 | 4.9 | 2.9 |
| 18.4 | 218.4 | 0.1 | 4.8 | 2.4 |
| 23.4 | 151.2 | 0.2 | 3.8 | 1.7 |
| 24.7 | 598.6 | 0.1 | 3.6 | 6.6 |
| 25.4 | 59.4 | 0.2 | 3.5 | 0.7 |
| 29.5 | 52.4 | 0.4 | 3.0 | 0.6 |
| 31.1 | 197.0 | 0.1 | 2.9 | 2.2 |
| 33.9 | 45.1 | 0.2 | 2.6 | 0.5 |
| 37.5 | 59.4 | 0.2 | 2.4 | 0.7 |

Compound 1 Besylate exhibits a DSC thermogram having endotherm peaks at temperatures of about 52° C. and about 138° C. Compound 1 Besylate shows a weight loss of about 5.2% when heated to 150° C. FIG. 9 shows a DSC thermogram and a TGA thermogram of Compound 1 Besylate.

Example A. Enzymatic Assay for Inhibition of PARP7

Displacement of Probe A, a biotinylated probe binding to the TIPARP active site, was measured using a time-resolved fluorescence energy transfer (TR-FRET) assay. 20 nL of a dose response curve of each test compound was spotted in black 384-well polystyrene proxiplates (Perkin Elmer) using a Mosquito (TTP Labtech). Reactions were performed in a 8 µL volume by adding 6 µL of TIPARP and Probe A in assay buffer (20 mM HEPES pH=8, 100 mM NaCl, 0.1% bovine serum albumin, 2 mM DTT and 0.002% Tween20), incubating with test compound at 25° C. for 30 min, then adding 2 µL of ULight-anti 6xHis and LANCE Eu-W1024 labeled streptavidin (Perkin Elmer). The final concentrations of TIPARP and Probe A were 6 nM and 2 nM, respectively. The final concentration of ULight-anti 6xHis and LANCE Eu-W1024 labeled streptavidin were 4 nM and 0.25 nM, respectively. Reactions were incubated at 25° C. for an additional 30 min, then read on an Envision platereader equipped with a LANCE/DELFIA top mirror (Perkin Elmer) using excitation of 320 nm and emission of 615 nm and 665 nM with a 90 us delay. The ratio of the 665/615 nm emission were calculated for each well to determine the amount of complex of TIPARP and Probe A in each well Control wells containing a negative control of 0.25% DMSO vehicle or a positive control of 100 µM Example 190 were used to calculate the % a inhibition as described below:

$$\% \text{ Inhibition} = 100 \times \frac{TRF_{cmpd} - TRF_{min}}{TRF_{max} - TRF_{min}}$$

where $TRF_{cmpd}$ is the TR-FRET ratio from the compound treated well, $TRF_{min}$ is the TR-FRET ratio from the Example 190-treated positive control well and $TRF_{max}$ is the TR-FRET ratio from the DMSO-treated negative control well.

The % inhibition values were plotted as a function of compound concentration and the following 4-parameter fit was applied to derive the IC$_{50}$ values:

$$Y = \text{Bottom} + \frac{(\text{Top} - \text{Bottom})}{(1 + \left(\frac{X}{IC_{50}}\right)^{\text{Hill Coefficient}})}$$

where top and bottom are normally allowed to float, but may be fixed at 100 or 0 respectively in a 3-parameter fit. The Hill Coefficient is normally allowed to float but may also be fixed at 1 in a 3-parameter fit. Y is the % inhibition and X is the compound concentration.

Synthesis of Probe A

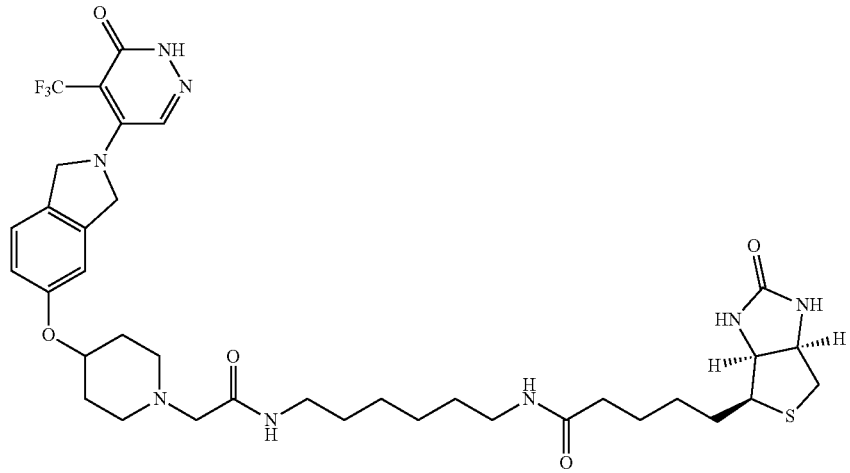 [SMILES: O=C(CCCC[C@@H]1SC[C@@H]2NC(=O)N[C@@H]21)NCCCCCCNC(=O)CN1CCC(Oc2ccc3c(c2)CN(c2cn[nH]c(=O)c2C(F)(F)F)C3)CC1]

Step 1: 5-(5-Hydroxy-2,3-dihydro-1H-isoindol-2-yl)-4-(trifluoromethyl)-2-[[2-(trimethylsilyl)ethoxy]methyl]-2,3-dihydropyridazin-3-one A solution of 5-chloro-4-(trifluoromethyl)-2-[[2-(trimethylsilyl)ethoxy]methyl]-2,3-dihydropyridazin-3-one (2.8 g, 8.52 mmol, 1.00 equiv), 2,3-dihydro-1H-isoindol-5-ol hydrobromide (4.27 g, 19.76 mmol, 1.00 equiv), and TEA (10 mL) in ethanol (40 mL) was stirred for 1 h at 60° C. The resulting solution was extracted with 2×100 mL of ethyl acetate and the organic layers combined and concentrated under reduced pressure to afford 4.5 g of the title compound as a yellow oil. LCMS: [M+H]+ 428.23.

Step 2: tert-Butyl 4-([2-[6-oxo-5-(trifluoromethyl)-4-[[2-(trimethylsilyl)ethoxy]methyl]-1,6-dihydro-pyridazin-4-yl]-2,3-dihydro-1H-isoindol-5-yl]oxy)piperidine-1-carboxylate A solution of 5-(5-hydroxy-2,3-dihydro-1H-isoindol-2-yl)-4-(trifluoromethyl)-2-[[2-(trimethylsilyl)ethoxy]methyl]-2,3-dihydropyridazin-3-one (4.5 g, 10.53 mmol, 1.00 equiv), tert-butyl 4-iodopiperidine-1-carboxylate (20 g, 64.28 mmol, 8.00 equiv), potassium carbonate (15 g, 108.53 mmol, 10.00 equiv), and DMF (50 mL) was stirred for 2 days at 80° C. The resulting solution was extracted with 2×200 mL of ethyl acetate and the organic layers combined and concentrated under reduced pressure. The residue was applied onto a silica gel column eluting with ethyl acetate/petroleum ether to afford the title compound (2 g, 31%) as a yellow oil. LCMS: [M+H]+ 611.15.

Step 3: 5-[5-(Piperidin-4-yloxy)-2,3-dihydro-1H-isoindol-2-yl]-4-(trifluoromethyl)-2-[[2-(trimethylsilyl)ethoxy]methyl]-2,3-dihydropyridazin-3-one A solution of tert-butyl 4-([2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidine-1-carboxylate (2 g, 3.27 mmol, 1.00 equiv), dioxane/HCl (5 mL), and dioxane (45 mL) was stirred for 6 h at 25° C. The resulting mixture was concentrated under reduced pressure. The residue was applied onto a silica gel column and eluted with ethyl acetate/petroleum ether to afford 1 g of title compound as a yellow oil. LCMS: [M+H]+ 511.28.

Step 4: tert-Butyl 2-[4-([2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidin-1-yl]acetate A solution of 5-[5-(piperidin-4-yloxy)-2,3-dihydro-1H-isoindol-2-yl]-4-(trifluoromethyl)-2-[[2-(trimethylsilyl)ethoxy]methyl]-2,3-dihydropyridazin-3-one (1 g, 1.96 mmol, 1.00 equiv), tert-butyl 2-chloroacetate (450 mg, 2.99 mmol, 3.00 equiv), DIPEA (5 mL), and dichloromethane (10 mL) was stirred overnight at 25° C. The residue was purified by C18 reverse phase chromatography eluting with H2O/CH3CN to afford the title compound (540 mg, 44%) as a yellow oil. LCMS: [M+H]+ 625.20.

Step 5: 2-[4-([2-[6-Oxo-5-(trifluoromethyl)-1,6-dihydropyridazin-4-yl]-2,3-dihydro-1H-isoindol-5-yl]oxy)piperidin-1-yl]hydrochloride A solution of tert-butyl 2-[4-([2-[6-oxo-5-(trifluoromethyl)-1-[[2-(trimethylsilyl)ethoxy]methyl]-1,6-dihydro-pyridazin-4-yl]-2,3-dihydro-1H-isoindol-5-yl]oxy)piperidin-1-yl]acetate (540 mg, 0.86 mmol, 1.00 equiv) and dioxane/HCl (8 mL) was stirred overnight at 25° C. The resulting mixture was concentrated under reduced pressure. The residue was purified by C18 reverse phase chromatography eluting with H2O/CH3CN to afford 200 mg (53%) of title compound as a white solid. LCMS: [M+H]+ 439.31.

Step 6: Tert-butyl N-(6-[5-[(3aS,4S,6aR)-2-oxo-hexahydro-1H-thieno[3,4-d]imidazolidin-4-yl]pentanamido]hexyl)carbamate A solution of 5-[(3aS,4S,6aR)-2-oxo-hexahydro-1H-thieno[3,4-d]imidazolidin-4-yl]pentanoic acid (reagent was purchased from Beijing Dragon Rui Trading Company, 976 mg, 3.99 mmol, 1.00 equiv), DIPEA (1.55 g, 11.99 mmol, 3.00 equiv), HATU (1.82 g, 4.79 mmol, 1.20 equiv), tert-butyl N-(6-aminohexyl)carbamate (864 mg, 3.99 mmol, 1.00 equiv) in DMF (15 mL) was stirred overnight at 25° C. The reaction was then quenched by the addition of 50 mL of water. The solids were collected by filtration to afford 1.5 g (85%) of the title compound as a white solid. LCMS: [M+H]$^+$ 443.26.

Step 7: 5-[(3aS,4S,6aR)-2-Oxo-hexahydro-1H-thieno[3,4-d]imidazolidin-4-yl]-N-(6-aminohexyl) pentanamide hydrochloride A solution of tert-butyl N-(6-[5-[(3aS,4S,6aR)-2-oxo-hexahydro-1H-thieno[3,4-d]imidazolidin-4-yl]pentanamido]hexyl)carbamate (800 mg, 1.81 mmol, 1.00 equiv) in hydrogen chloride/dioxane (20 mL) was stirred overnight at 25° C. The resulting mixture was concentrated under reduced pressure to afford 600 mg (88%) of the title compound as a gray crude oil. LCMS: [M+H]$^+$ 343.21.

Step 8: 5-[(3aS,4S,6aR)-2-Oxo-hexahydro-1H-thieno[3,4-d]imidazolidin-4-yl]-N-(6-[2-[4-([2-[6-oxo-5-(trifluoromethyl)-1,6-dihydropyridazin-4-yl]-2,3-dihydro-1H-isoindol-5-yl]oxy)piperidin-1-yl] acetamido]hexyl)pentanamide A solution of 2-[4-([2-[6-oxo-5-(trifluoromethyl)-1,6-dihydropyridazin-4-yl]-2,3-dihydro-1H-isoindol-5-yl]oxy)piperidin-1-yl]hydrochloride (175 mg, 0.40 mmol, 1.00 equiv), DIPEA (258 mg, 2.00 mmol, 5.00 equiv), HATU (228 mg, 0.60 mmol, 1.50 equiv), 5-[(3aS,4S,6aR)-2-oxo-hexahydro-1H-thieno[3,4-d]imidazolidin-4-yl]-N-(6-aminohexyl)pentanamide hydrochloride (228 mg, 0.60 mmol, 1.50 equiv) in DMF (3 mL) was stirred for 4 h at 25° C. The crude product was purified by C18 reverse phase chromatography eluting with H$_2$O/CH$_3$CN to afford the title compound as a white solid (118.3 mg, 39%). LCMS: [M+H]$^+$ 763.35.

$^1$H NMR (DMSO-d$_6$, 400 MHz) δ: 12.52 (s, 1H), 7.98 (s, 1H), 7.81-7.68 (m, 2H), 7.26 (d, J=8.4 Hz, 1H), 7.00 (d, J=2.2 Hz, 1H), 6.91 (dd, J=8.4, 2.3 Hz, 1H), 6.45-6.39 (m, 1H), 6.36 (s, 1H), 4.91 (d, J=6.1 Hz, 4H), 4.45 (m, 1H), 4.26 (m, 1H), 4.17-4.08 (m, 1H), 3.14-2.96 (m, 5H), 2.91 (s, 2H), 2.82 (dd, J=12.4, 5.1 Hz, 1H), 2.73-2.63 (m, 2H), 2.58 (d, J=12.4 Hz, 1H), 2.33 (ddd, J=11.8, 9.4, 3.1 Hz, 2H), 2.11-1.90 (m, 4H), 1.76-1.54 (m, 3H), 1.57-1.20 (m, 13H).

The IC$_{50}$ of Compound 1 was measured to be less than 0.1 μM in the TR-FRET assay for inhibition of PARP7, described above.

Example B: Inhibition of Cancer Cell Growth by Treatment with Compound 1

Table 17 represents the concentration that causes 50% growth inhibition (GI$_{50}$) in a panel of cancer cell lines with Compound 1. Cells were plated into 384-well plates at a pre-specified density in fetal bovine serum-containing media. Cells were treated with compound or vehicle (DMSO) 24 hrs later, and a day zero plate was collected for analysis. Test compound plates were incubated continuously for 144 hours before cells and cell growth was assessed using a luminescent cell viability assay (CellTiter-Glo, Promega). The GI$_{50}$ was determined by correcting for the cell count at time zero (time of treatment) and plotting data as percent growth relative to vehicle-treated cells.

GI$_{50}$ data for Compound 1 is provided below in Table 17 ("+" is <0.1 μM; "++" is ≥0.1 μM and <1 μM; and "+++" is ≥1 μM).

TABLE 17

Growth Inhibition in Different Cancer Cell Lines with Compound 1.

| Cell Line | Cancer Type | Compound 1 GI$_{50}$ |
|---|---|---|
| TYK-nu | high grade ovarian serous adenocarcinoma | + |
| Caki-1 | clear cell renal cell carcinoma | + |
| SCC-25 | tongue squamous cell carcinoma | + |
| GCT | undifferentiated pleiomorphic sarcoma | + |
| NCI-H647 | lung adenosquamous carcinoma | + |
| NCI-H1373 | lung adenocarcinoma | + |
| EBC-1 | squamous cell lung carcinoma | + |
| NCI-H2347 | lung adenocarcinoma | + |
| Panc 03.27 | pancreatic adenocarcinoma | + |
| HCC827 | lung adenocarcinoma | + |
| TUHR10TKB | renal cell carcinoma | + |
| IA-LM | large cell lung carcinoma | + |
| CFPAC-1 | pancreatic ductal adenocarcinoma | ++ |
| COR-L105 | lung adenocarcinoma | ++ |
| SW900 | squamous cell lung carcinoma | ++ |
| NCI-H2066 | squamous cell lung carcinoma | +++ |
| TE-11 | esophageal squamous cell carcinoma | +++ |
| MSTO-211H | biphasic mesothelioma | +++ |
| NCI-H2009 | lung adenocarcinoma | +++ |
| SK-LU-1 | lung adenocarcinoma | +++ |
| NCI-H2087 | lung adenocarcinoma | +++ |
| NCI-H1930 | small cell lung carcinoma | +++ |
| H4 | neuroglioma | +++ |
| LN-18 | glioblastoma | +++ |
| CAL-27 | tongue squamous cell carcinoma | +++ |
| A101D | melanoma | +++ |
| ACC-MESO-1 | mesothelioma | +++ |
| AGS | gastric adenocarcinoma | +++ |
| COLO 680N | esophageal squamous cell carcinoma | +++ |
| HCC1954 | ductal breast carcinoma | +++ |
| HPAF-II | pancreatic adenocarcinoma | +++ |
| HT-1080 | fibrosarcoma | +++ |
| KALS-1 | glioblastoma | +++ |
| KMBC-2 | bladder carcinoma | +++ |
| KMRC-3 | clear cell renal carcinoma | +++ |
| MCAS | ovarian mucinous cystadenocarcinoma | +++ |
| MDA-MB-468 | breast adenocarcinoma | +++ |
| NCI-H1437 | lung adenocarcinoma | +++ |
| NCI-H1648 | lung adenocarcinoma | +++ |
| NCI-H1944 | lung adenocarcinoma | +++ |
| NCI-H1963 | small cell lung carcinoma | +++ |
| NCI-H2291 | lung adenocarcinoma | +++ |
| NCI-H2444 | non-small cell lung carcinoma | +++ |
| NCI-H441 | papillary adenocarcinoma of the lung | +++ |
| NUGC-3 | gastric adenocarcinoma | +++ |
| SCaBER | bladder squamous cell carcinoma | +++ |
| SF126 | glioblastoma multiforme | +++ |
| SK-MEL-2 | malignant melanoma | +++ |
| SK-MES-1 | squamous cell lung carcinoma | +++ |
| SNU-840 | malignant ovarian Brenner tumor | +++ |
| T84 | colon adenocarcinoma | +++ |
| YD-10B | tongue squamous cell carcinoma | +++ |

Example C: Inhibition of Tumor Growth by Oral Dosing with Compound 1

The effect of Compound 1 on tumor growth was studied in a human NCI-H1373 lung cancer xenograft and a murine CT26 colon cancer syngeneic model.

Figure 10:
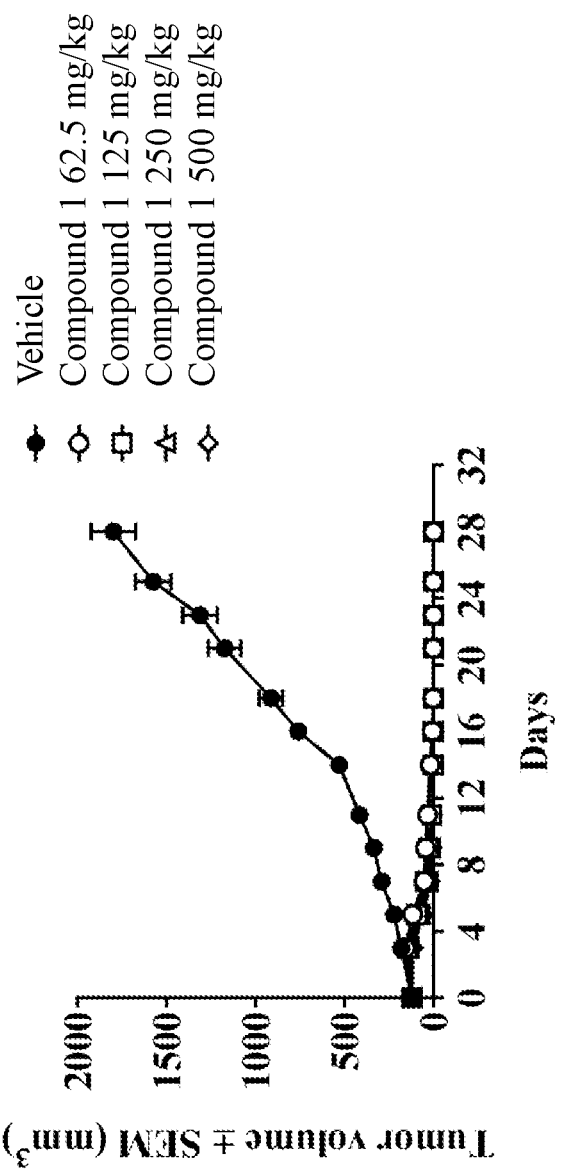
FIG. 10 illustrates that once daily administration of PARP7 inhibitor Compound 1 significantly reduces tumor growth in a human NCI-H1373 lung cancer xenograft.

For the NCI-H1373 study, SCID mice were inoculated subcutaneously in the right flank with NCI-H1373 cells for tumor development. After 5 days of tumor growth, mice with 89-148 mm³ tumors were randomized into treatment groups with mean tumor volumes of 121 mm³. The treatments were started from the next day post randomization (defined randomization day as day 0) and were treated with vehicle (50% Labrasol) or Compound 1 (62.5, 125, 250, and 500 mg/kg) once a day for 28 days by oral gavage. Tumor volumes were determined by manual calipers every 2-3 days. Mean tumor volume and SEM are plotted. QD: once a day; PO: per oral administration. Statistical significance is calculated using two-way ANOVA followed by Bonferroni post-tests in which the treatment groups were compared to vehicle control (****P<0.0001). FIG. 10 illustrates that once daily administration of PARP7 inhibitor Compound 1 significantly reduces tumor growth in a human NCI-H1373 lung cancer xenograft. In the mouse NCI-H1373 human lung cancer cell model, Compound 1 at doses of 62.5 to 500 mg/kg administered once a day for 28 days caused complete tumor regression at all dose levels.

Figure 11:
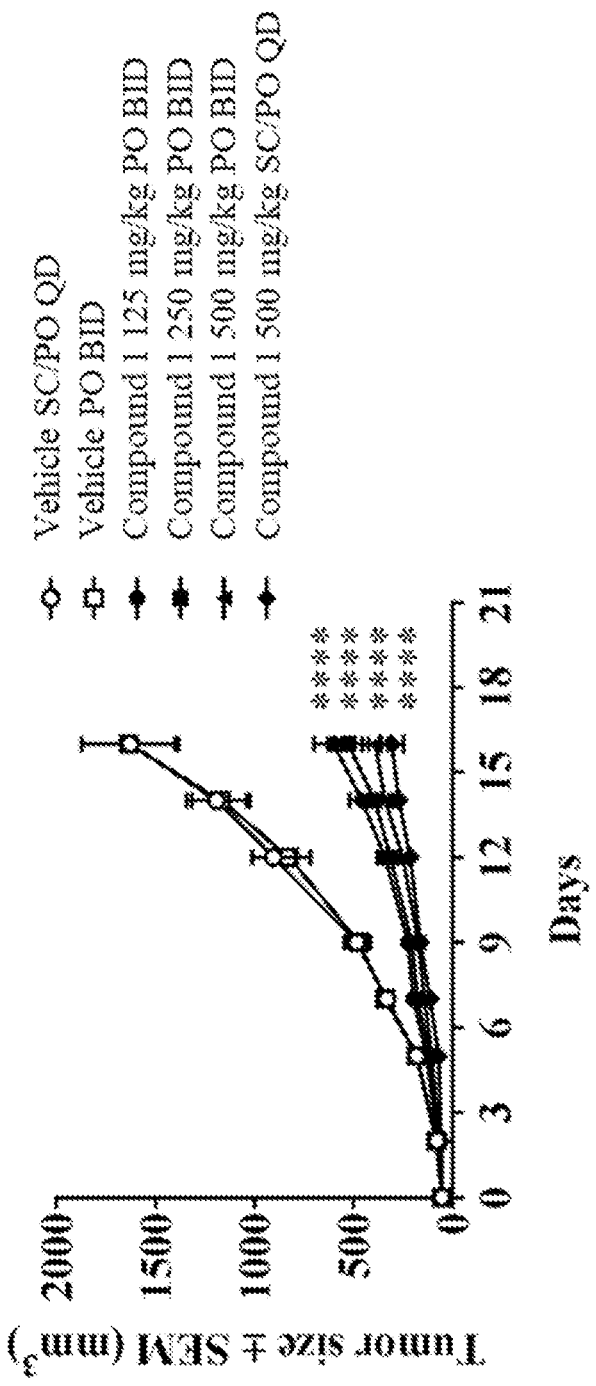
FIG. 11 illustrates that once or twice daily administration of PARP7 inhibitor Compound 1 significantly reduces tumor growth in a murine CT26 colon cancer syngeneic model.

For the CT26 study, BALB/c mice were inoculated subcutaneously in the right flank with CT26 cells for tumor development. After 5 days of cell inoculation, mice with 36-79 mm³ tumors were randomized into treatment groups with mean tumor volumes of 54 mm³. The treatments were started from the next day post randomization (defined randomization day as day 0) and were treated with vehicle (25 or 50% Labrasol) or Compound 1 BID (2 times a day every 12 hours) at doses ranging from 125-500 mg/kg or QD (once a day) at 500 mg/kg for 21 days by oral gavage or needle subcutaneously. Tumor volumes were determined by manual calipers every 2-3 days. Mean tumor volume and SEM are plotted. BID: twice a day; PO: per oral administration; QD: once a day; SC: per subcutaneous administration. The first two doses for vehicle and Compound 1 500 mg/kg in the QD groups were delivered by subcutaneous injection. Statistical analysis for tumor growth inhibition (TGI) was performed when at least 8 of the 10 mice were remaining in the vehicle group (Day 16). Statistical significance is calculated using two-way ANOVA followed by Bonferroni post-tests in which the treatment groups were compared to vehicle control (**** P<0.0001). FIG. 11 illustrates that once or twice daily administration of PARP7 inhibitor Compound 1 significantly reduces tumor growth in a murine CT26 colon cancer syngeneic model.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A solid form of Compound 1 having the formula:

Compound 1 wherein the solid form has crystalline Form B, and wherein the solid form has characteristic XRPD peaks at about 5.7, about 11.3, about 14.1, and about 16.9 degrees 2-theta.

2. The solid form of claim 1, having an XRPD pattern with characteristic peaks as substantially shown in FIG. 4.

3. The solid form of claim 1, having a DSC thermogram comprising endotherm peaks at temperatures of about 71° C., about 83° C., about 100° C., and about 172° C.

4. The solid form of claim 1, having a DSC thermogram substantially as depicted in FIG. 5.

5. A solid form of Compound 1 having the formula:

Compound 1 wherein the solid form has crystalline Form C, and wherein the solid form has characteristic XRPD peaks at about 16.6, about 18.8, and about 21.6 degrees 2-theta.

6. The solid form of claim 5, having an XRPD pattern with characteristic peaks as substantially shown in FIG. 6.

7. The solid form of claim 5, having a DSC thermogram comprising endotherm peaks at temperatures of about 159° C. and about 174° C.

8. The solid form of claim 5, having a DSC thermogram substantially as depicted in FIG. 7.

9. A salt which is a benzenesulfonic acid salt of Compound 1 having the formula:

Compound 1

10. The salt of claim 9 which is crystalline.

11. The salt of claim 10, having at least one characteristic XRPD peak selected from about 5.8 and about 6.2 degrees 2-theta.

12. The salt of claim 10, having characteristic XRPD peaks at about 5.8 and about 6.2 degrees 2-theta.

13. The salt of claim 10, having an XRPD pattern with characteristic peaks as substantially shown in FIG. 8.

14. The salt of claim 10, having a DSC thermogram comprising endotherm peaks at temperatures of about 52° C. and about 138° C.

15. The salt of claim 10, having a DSC thermogram substantially as depicted in FIG. 9.

16. The salt of claim 10 which is hydrated or solvated.

17. A pharmaceutical composition comprising a solid form of claim 1 or 5, or a salt of claim 9, and at least one pharmaceutically acceptable carrier.

18. A method of inhibiting the activity of PARP7 comprising contacting a solid form of claim 1 or 5, or a salt of claim 9, with said PARP7.

19. A method of treating cancer in a patient in need of treatment comprising administering to said patient a therapeutically effective amount of a solid form of claim 1 or 5, or a salt of claim 9.

20. The method of claim 19 wherein said cancer is breast cancer, cancer of the central nervous system, endometrium cancer, kidney cancer, large intestine cancer, lung cancer, oesophagus cancer, ovarian cancer, pancreatic cancer, prostate cancer, stomach cancer, head and neck cancer upper aerodigestive cancer, urinary tract cancer, or colon cancer.

* * * * *